(12) United States Patent
Victorine et al.

(10) Patent No.: US 8,918,157 B2
(45) Date of Patent: Dec. 23, 2014

(54) CRIMP TERMINATIONS FOR CONDUCTORS IN IMPLANTABLE MEDICAL LEAD AND METHOD OF MAKING SAME

(71) Applicant: Pacesetter, Inc., Sylmar, CA (US)

(72) Inventors: Keith Victorine, Santa Clarita, CA (US); Steven R. Conger, Agua Dulce, CA (US); Greg Kampa, Laguna Nigel, CA (US); Dorab N. Sethna, Culver City, CA (US); Daniel Ephraim, North Hills, CA (US); Sean Matthew Desmond, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/052,020

(22) Filed: Oct. 11, 2013

(65) Prior Publication Data

US 2014/0074209 A1 Mar. 13, 2014

Related U.S. Application Data

(62) Division of application No. 12/716,552, filed on Mar. 3, 2010, now Pat. No. 8,594,761.

(51) Int. Cl.
*A61N 1/05* (2006.01)
*H01R 43/00* (2006.01)
*H01R 43/048* (2006.01)

(52) U.S. Cl.
CPC *A61N 1/05* (2013.01); *H01R 43/00* (2013.01); *H01R 43/048* (2013.01)
USPC .............. 600/373; 607/1; 607/2; 607/115; 607/116; 600/372; 600/377

(58) Field of Classification Search
USPC ........... 607/1–2, 115–116; 600/372–373, 377
See application file for complete search history.

(56) References Cited

U.S. PATENT DOCUMENTS

| 5,569,220 A | 10/1996 | Webster, Jr. |
| 5,591,142 A | 1/1997 | Van Erp |
| 8,170,691 B2 | 5/2012 | Eckerdal |

FOREIGN PATENT DOCUMENTS

WO 2008133533 A1 11/2008

OTHER PUBLICATIONS

Restriction Requirement, mailed Aug. 20, 2012—Parent U.S. Appl. No. 12/716,552.
NonFinal Office Action, mailed Nov. 2, 2012—Parent U.S. Appl. No. 12/716,552.
Notice of Allowance, mailed Sep. 9, 2013—Parent U.S. Appl. No. 12/716,552.

*Primary Examiner* — Deborah Malamud

(57) ABSTRACT

A method of manufacturing an implantable medical lead is disclosed herein. The method may include: providing a lead body including a proximal end, a distal end, and an electrode near the distal end; provide a conductor extending between the proximal and distal ends; providing a crimp including a ribbon-like member and extending the ribbon-like member around the conductor; and mechanically and electrically connecting the ribbon-like member to the electrode.

3 Claims, 35 Drawing Sheets

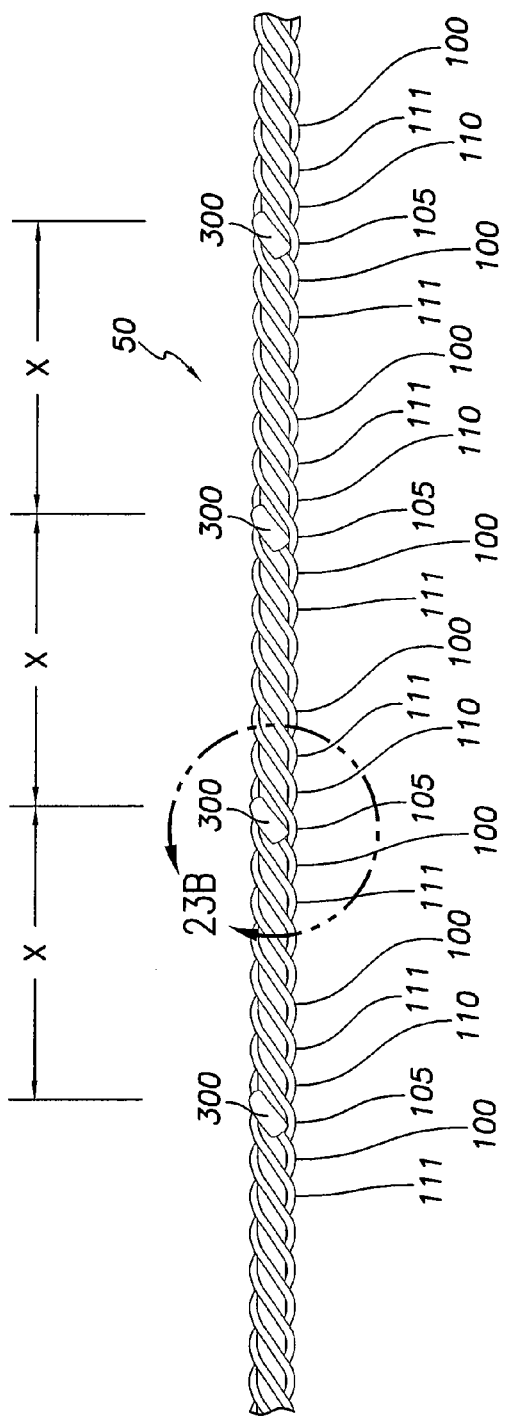
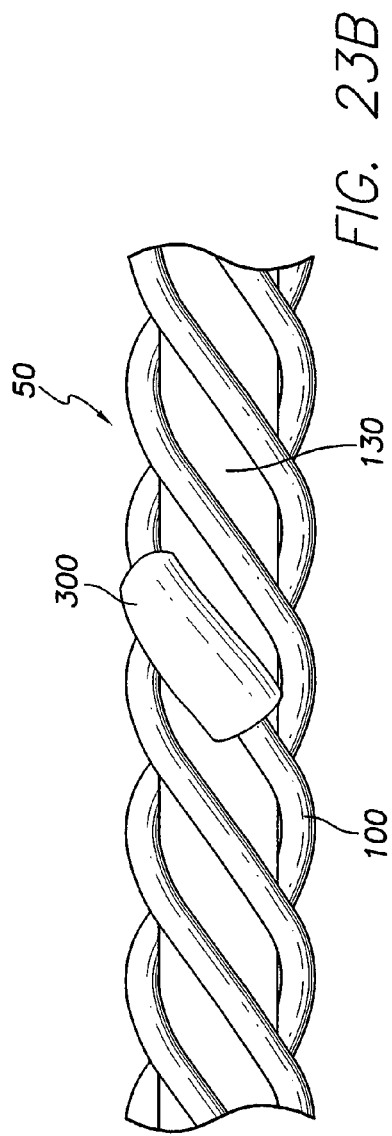
FIG. 23A
FIG. 23B

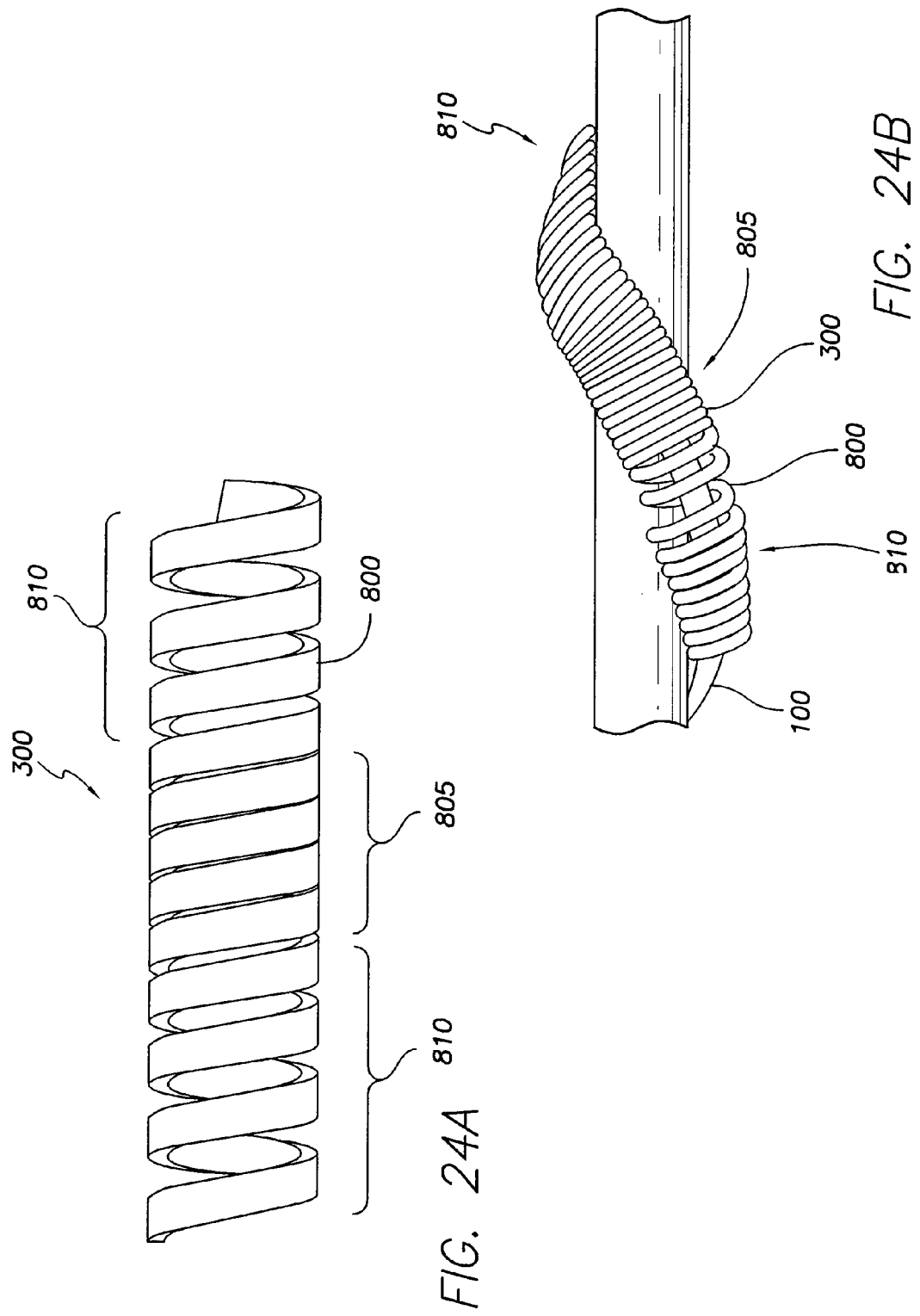

CRIMP TERMINATIONS FOR CONDUCTORS IN IMPLANTABLE MEDICAL LEAD AND METHOD OF MAKING SAME

CROSS REFERENCE TO RELATED APPLICATIONS

This application is a divisional of U.S. patent application Ser. No. 12/716,552, filed Mar. 3, 2010, now U.S. Pat. No. 8,594,761, and related to:
1) Ser. No. 14/051,764, titled "Crimp Terminations for Conductors in Implantable Medical Lead and Method of Making Same";
2) Ser. No. 14/051,795, titled "Crimp Terminations for Conductors in Implantable Medical Lead and Method of Making Same";
3) Ser. No. 14/051,829, titled "Crimp Terminations for Conductors in Implantable Medical Lead and Method of Making Same";
4) Ser. No. 14/051,850, titled "Crimp Terminations for Conductors in Implantable Medical Lead and Method of Making Same";
5) Ser. No. 14/051,877, titled "Crimp Terminations for Conductors in Implantable Medical Lead and Method of Making Same";
6) Ser. No. 14/051,976, titled "Crimp Terminations for Conductors in Implantable Medical Lead and Method of Making Same";
7) Ser. No. 14/051,995, titled "Crimp Terminations for Conductors in Implantable Medical Lead and Method of Making Same";
8) Ser. No. 14/052,042, titled "Crimp Terminations for Conductors in Implantable Medical Lead and Method of Making Same"; all applications filed Oct. 11, 2014.
8) Ser. No. 14/052,042, titled "Crimp Terminations for Conductors in Implantable Medical Lead and Method of Making Same";
all applications filed Oct. 11, 2013.

FIELD OF THE INVENTION

The present invention relates to medical apparatus and methods. More specifically, the present invention relates to implantable medical leads and methods of manufacturing such leads.

BACKGROUND OF THE INVENTION

Implantable pulse generators, such as pacemakers, defibrillators, implantable cardioverter defibrillators ("ICD") and neurostimulators, provide electrotherapy via implantable medical leads to nerves, such as those nerves found in cardiac tissue, the spinal column, the brain, etc. Electrotherapy is provided in the form of electrical signals, which are generated in the pulse generator and travel via the lead's conductors to the electrotherapy treatment site.

Patients may benefit from electrotherapy treatments to be proposed in the future. However, current conventional lead manufacturing technology has generally limited the extent to which leads can be reduced in size and the elements or features that can be carried on leads.

There is a need in the art for a lead having a configuration that allows the lead to have a reduced size and which is capable of supporting elements or features in a variety of configurations. There is also a need in the art for a method of manufacturing such a lead.

BRIEF SUMMARY OF THE INVENTION

Disclosed herein is an implantable medical lead. In one embodiment, the lead may include a longitudinally extending body, a helical anchor and a lead connector end. The longitudinally extending body may include a distal end, a proximal end, a braid-reinforced inner tubular layer extending between the proximal and distal ends, and an outer tubular layer extending between the proximal and distal ends. The braid-reinforced inner tubular layer may extend through the outer tubular layer in a coaxial arrangement. The helical anchor electrode may be operably coupled to a distal end of the braid-reinforced inner tubular layer. The lead connector end may be operably coupled to the proximal end of the body and include a pin contact operably coupled to a proximal end of the braid-reinforced tubular layer. Rotation of the pin contact relative to the lead connector end may cause rotation of the braid-reinforced inner tubular layer within the outer tubular layer, and the resulting rotation of the braid-reinforced inner tubular layer may cause rotation of the helical anchor electrode.

Another implantable medical lead is also disclosed herein. In one embodiment, the lead includes a longitudinally extending body having a distal end, a proximal end, and a braid-reinforced tubular layer extending between the proximal and distal ends. The braid-reinforced tubular layer may include a braid arrangement imbedded in a polymer wall material. The braid arrangement may include first and second conductors and first and second ribbons. The conductors and ribbons may be helically cross wound with each other such that the conductors do not cross each other and the ribbons do not cross each other.

Also disclosed herein is a method of assembling an implantable medical lead. In one embodiment, the method includes: providing a first longitudinally extending tubular liner including an outer circumferential surface; providing a first braid arrangement over the outer circumferential surface of the first longitudinally extending tubular liner, wherein the first braid arrangement includes first and second conductors and first and second ribbons, wherein the conductors and ribbons of the first braid arrangement are helically cross wound with each other such that the conductors do not cross each other and the ribbons do not cross each other; reflowing or molding (e.g., liquid injection mold ("LIM")) a first polymer material over the first braid arrangement and outer circumferential surface of the first longitudinally extending tubular liner such that the braid arrangement is substantially imbedded in the polymer material and the polymer material substantially adheres to the outer circumferential surface, resulting in a first braid-reinforced tubular layer; and electrically connecting the first conductor to an electrode.

Another implantable medical lead is also disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp including a collar and a tail extending from the collar. The collar includes a hole. The tail extends around the electrical conductor and through the hole. The crimp is electrically and mechanically coupled to the electrode.

Yet another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes opposed first and second portions that are each generally shaped like a half-cylinder. The portions are joined along a common longitudinal side. A tail extends from a free longitudinal side of the first portion. A hole is defined in the second portion. The tail extends around the electrical conductor and through the hole. The crimp is electrically and mechanically coupled to the electrode.

Yet another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a ribbon having a first end and a second end. The ribbon extends around the conductor. A first length of the ribbon near the first end is in contact with a second length of the ribbon near the second end. The crimp is electrically and mechanically coupled to the electrode.

Another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a portion and a tail extending from the portion, the portion having a generally half-cylinder shape that defines a trough. The conductor is received in the trough. The tail is electrically and mechanically coupled to the electrode.

Another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a generally cylindrical shape, a split extending generally longitudinally along the generally cylindrical shape, a hole in the generally cylindrical shape opposite the split, and a trough in which the conductor is received. The crimp is electrically and mechanically coupled to the electrode.

Yet another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a spherical outer surface and a recess formed in the spherical outer surface. The conductor is received in the recess, the crimp electrically and mechanically coupled to the electrode.

Yet another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a cylindrical outer surface, a pair of recesses formed in the cylindrical outer surface, and another recess formed in an end of the crimp. The conductor is received in the another recess, and the crimp is electrically and mechanically coupled to the electrode.

Another implantable medical lead is disclosed herein. In one embodiment, the lead includes a longitudinally extending body including a distal end and a proximal end, an electrode on the body near the distal end, a lead connector end operably coupled to the proximal end of the body, an electrical conductor extending between the lead connector end and the electrode, and a crimp. The crimp includes a helical shaped outer surface and a helically shaped opening extending through the length of the crimp. The conductor extends through the helically shaped opening. The crimp is electrically and mechanically coupled to the electrode.

Yet another implantable medical lead is disclosed herein. In one embodiment, the lead includes a longitudinally extending body including a distal end and a proximal end, a ring electrode on the body near the distal end, a lead connector end operably coupled to the proximal end of the body, an electrical conductor extending between the lead connector end and the electrode, and a crimp electrically and mechanically coupled to the electrode. The ring electrode includes a cylindrical wall and a seam extending proximal to distal along the wall. The seam is formed by a first wall edge extending proximal to distal and a second wall edge extending proximal to distal. The wall edges are opposed and brought together to form the seam. Each wall edge includes a notch such that, when the wall edges are brought together to form the seam, the notches form a window extending through the wall.

A method of manufacturing an implantable medical lead is also disclosed herein. In one embodiment the method includes: providing a lead body including a proximal end, a distal end, and an electrode near the distal end; provide a conductor extending between the proximal and distal ends; providing a crimp including a ribbon-like member and extending the ribbon-like member around the conductor; and mechanically and electrically connecting the ribbon-like member to the electrode.

Yet another method of manufacturing an implantable medical lead is disclosed herein. In one embodiment the method includes: providing a lead body including a proximal end and a distal end; providing a conductor extending between the proximal and distal ends; ablating a ringed recess in an outer surface of the lead body; providing a split ring electrode; threading the lead body through the split ring electrode when the split ring electrode is expanded; positioning the split ring electrode in the ringed recess; and mechanically and electrically connecting the ring electrode to the conductor.

A method of manufacturing an implantable medical lead is also disclosed herein. In one embodiment the method includes: providing a lead body including a proximal end, a distal end, and an electrode near the distal end; provide a conductor extending between the proximal and distal ends, the conductor including a helical crimp mounted on the conductor, the conductor extending through the helical crimp; and mechanically and electrically connecting the helical crimp to the electrode.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 23A and 23B are respectively, a side view of a lead body and an enlarged side view of the same lead body at a location of a crimp.

FIGS. 24A and 24B are, respectively, a plan view of a helical wound crimp and a plan view of the same crimp mounted on a conductor.

DETAILED DESCRIPTION

Figure 1:
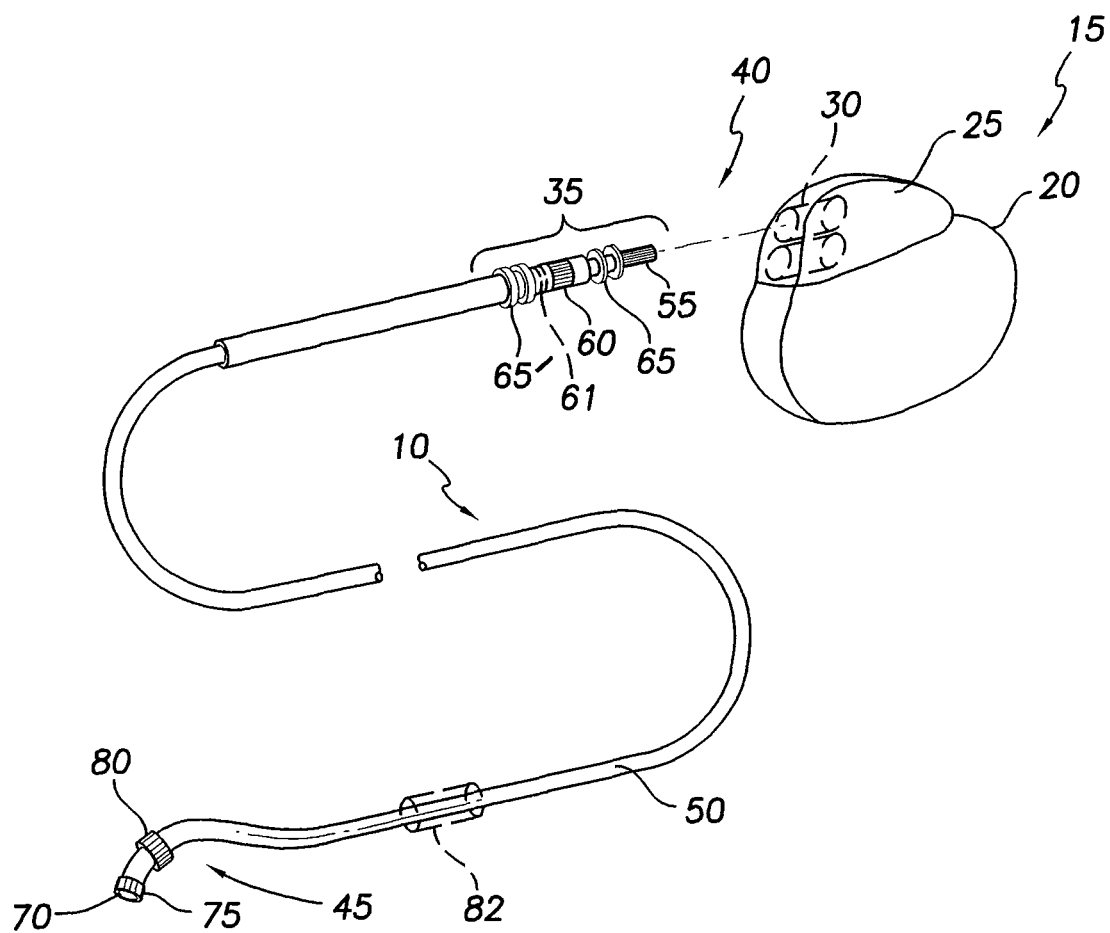
FIG. 1 is an isometric view of an implantable medical lead and a pulse generator for connection thereto.

An implantable medical lead 10 is disclosed herein. In one embodiment, the implantable medical lead 10 includes a tubular body 50 having one, two or more tubular layers 125, 135 each reinforced with a conductor/fiber braid arrangement 115 imbedded in the polymer material 162 forming the walls of the tubular layers 125, 135. The conductor/fiber braid arrangement 115 may be one, two or more helically wound conductors 100, 105, 110 woven with one, two or more helically wound fiber strips 165. In one embodiment, the braid arrangement 115 is such each conductor crosses the strips or ribbon 165, but does not cross itself or any other conductor. Similarly, each strip or ribbon 165 crosses the conductors, but does not cross itself or any of the strip or ribbon.

Such braid-reinforced layers 125, 135 offer the ability to manufacture lead bodies 50 have substantially reduced diameters, substantial improvement with respect to torque and flexibility consistency and capabilities, reduced manufacturing costs, and the ability to support a large number of electrodes and sensors in a large variety of configurations. Also, such braid-reinforced layers 135 may be used to replace the common helically wound central coil as a mechanism for extending/retracting a helical anchor electrode 85 and, in doing so, offer an anchor extension/retraction mechanism that provides one-to-one torque.

For a general discussion of an embodiment of a lead 10 including a body having at least one tubular layer reinforced with the conductor/fiber braid arrangement, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG. 1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. The proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. For example, the lead connector end 35 may be in the form of an IS-1, IS-4, DF-1, etc. configuration. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

Figure 2:
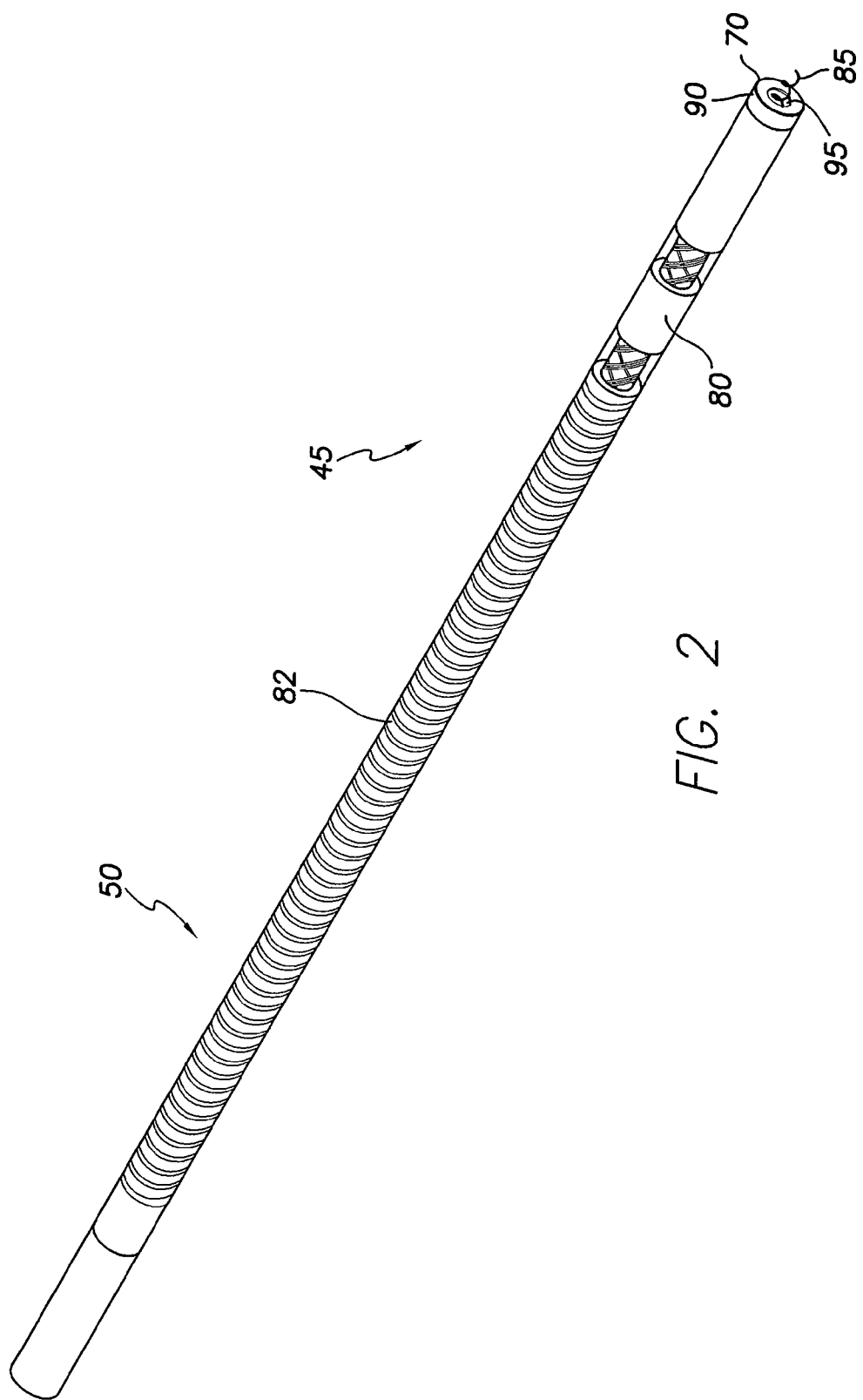
FIG. 2 is an isometric view of a distal portion of a tubular body of a medical lead similar to the lead depicted in FIG. 1, except the lead having an active fixation helical anchor at the lead distal end.

As illustrated in FIG. 1, in one embodiment, the lead distal end 45 may include a distal tip 70, a tip electrode 75 and a ring electrode 80. In some embodiments, as indicated in FIG. 2, which is an isometric view the distal end 45 of an alternative embodiment of the lead 10, the lead distal end 45 may include a helical anchor 85 that is extendable from within the distal tip 70 for active fixation and may or may not act as an electrode. In other embodiments, the lead distal end 45 may include features or a configuration that facilitates passive fixation.

As shown in FIGS. 1 and 2, in some embodiments, the distal end 45 may include a defibrillation coil 82 about the outer circumference of the lead body 50. The defibrillation coil 82 may be located proximal of the ring electrode 80.

As illustrated in FIG. 1 where the lead 10 is configured for passive fixation, the tip electrode 75 may form the distal tip 70 of the lead body 50. The ring electrode 80 may extend about the outer circumference of the lead body 50, proximal of the distal tip 70. In other embodiments, the distal end 45 may include a greater or lesser number of electrodes 75, 80 in different or similar configurations.

As indicated in FIG. 2 where the lead 10 is configured for active fixation, an atraumatic tip 90 may form the distal tip 70 of the lead body 50, and the helical anchor electrode 85 may be extendable/retractable relative to the distal tip 70 through an opening 95 in the distal tip 70. The ring electrode 80 may extend about the outer circumference of the lead body 50, proximal of the distal tip 70. In other embodiments, the distal end 45 may include a greater or lesser number of electrodes in different or similar configurations.

Figure 3:
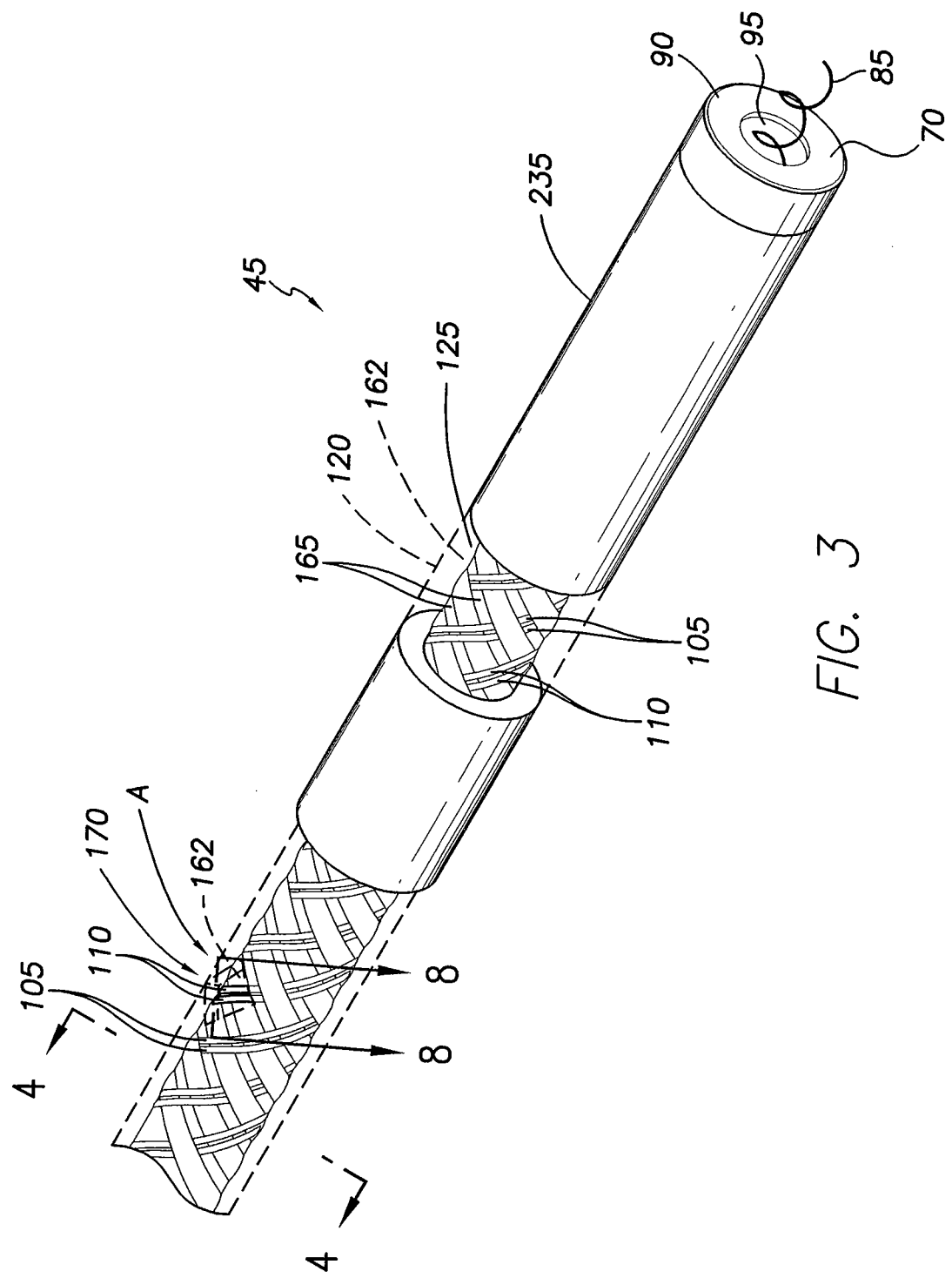
FIG. 3 is an enlarged isometric view of the distal portion of the tubular body of the medical lead of FIG. 2, except the shock coil is hidden and the outer circumferential surface of the outer tubular layer of the lead body is shown in phantom line for clarity purposes.

In one embodiment, the tip electrode 75 or helical anchor electrode 85 may be in electrical communication with the pin contact 55 via a first helically routed electrical conductor 100 (see FIGS. 9 and 10) and the ring electrode 80 may be in electrical communication with the first ring contact 60 via a second helically routed electrical conductor or pair of helically routed electrical conductors 105 (see FIGS. 2 and 3). In some embodiments, the defibrillation coil 82 may be in electrical communication with the second ring contact 61 via a third helically routed electrical conductor or pair of helically routed electrical conductors 110 (see FIGS. 2, 3 and 8). In yet other embodiments, other lead components (e.g., additional ring electrodes, various types of sensors, etc.) mounted on the lead body distal region 45 or other locations on the lead body 50 may be in electrical communication with a third ring contact (not shown) similar to the second ring contact 61 via a fourth helically routed electrical conductor or pair of helically routed electrical conductors. Of course, if needed, helically routed electrical conductors in addition to those already mentioned may be routed through the lead body in a manner similar to that depicted in FIGS. 2, 3, 9 and 10. Any of the helically routed conductors may be routed singly, in pairs, groups of three, groups of four, etc. Depending on the embodiment, any of the helically routed electrical conductors may be in the form of a multi-strand or filar cable or a solid wire conductor. Depending on the embodiment, any of the helically routed conductors may have a dedicated electrical insulation jacket or be jacketless such that the electrical conductor is reliant upon the material forming the tubular liner for electrical insulation.

Figure 4:
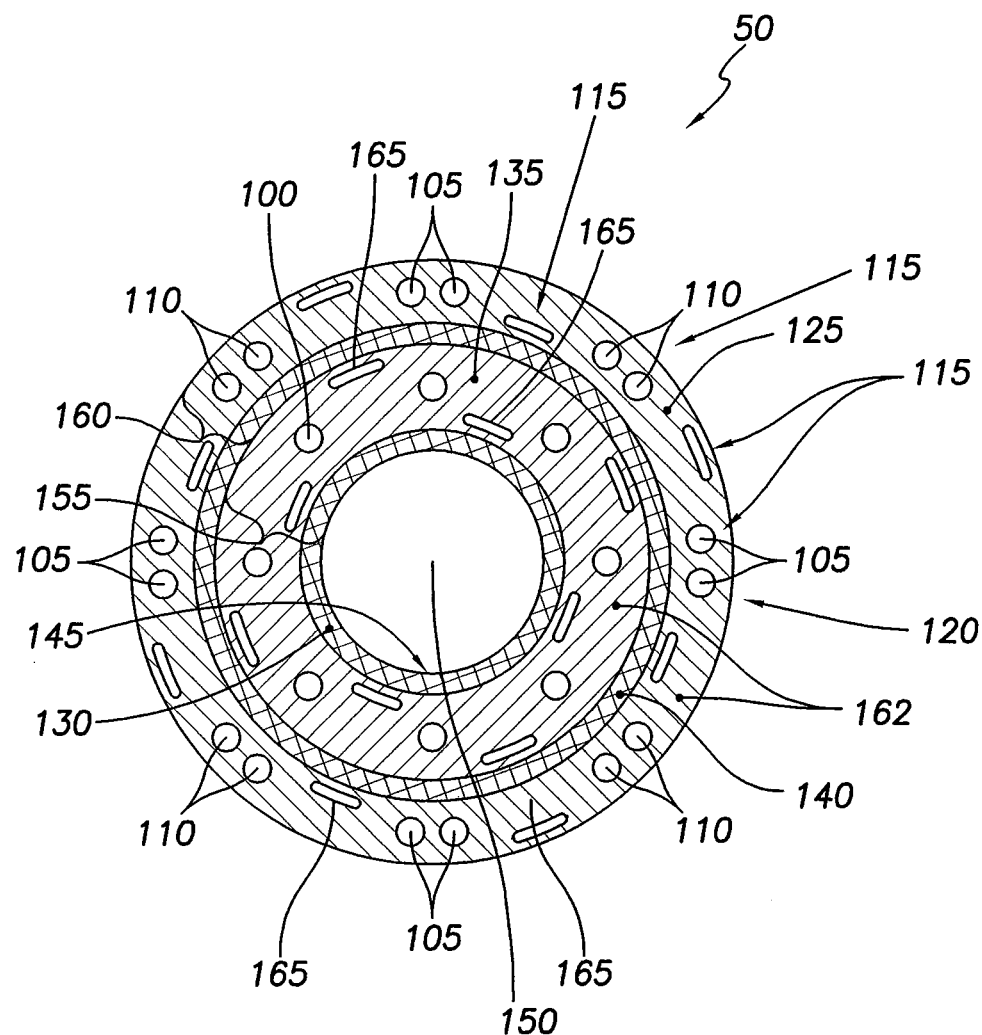
FIG. 4 is a transverse cross section of the tubular body of the medical lead as taken along section line 4-4 in FIG. 3.

For a detailed discussion regarding a lead body 50 employing the conductor/fiber braid arrangement 115 disclosed herein, reference is made to FIGS. 3 and 4. FIG. 3 is an enlarged isometric view of the distal end 45 of the tubular body 50 of the medical lead 10 of FIG. 2, except the shock coil 82 is hidden and the outer circumferential surface 120 of the outer tubular layer 125 of the lead body 50 is shown in phantom line for clarity purposes. FIG. 4 is a transverse cross section of the lead body 50 as taken along section line 4-4 in FIG. 3.

As shown in FIG. 4, in one embodiment, the tubular body 50 of the medical lead 10 may include an innermost tubular liner layer 130, an innermost tubular braid-reinforced layer 135, an outermost tubular liner layer 140 and an outermost tubular braid-reinforced layer 125. An inner circumferential surface 145 of the innermost liner layer 130 may define a central lumen 150 extending longitudinally through the tubular lead body 50. An outer circumferential surface of the innermost liner layer 130 may abut against the inner circumferential surface of the innermost braid-reinforced layer 135. An outer circumferential surface of the innermost braid-reinforced layer 135 may displaceably abut against the inner circumferential surface of the outermost liner layer 135 such that the innermost layer assembly 155 (i.e., the innermost liner layer 130 and the innermost braid-reinforced layer 135) may be caused to rotationally displace within the outermost layer assembly 160 (i.e., the outermost liner layer 140 and the outermost braid-reinforced layer 125). An outer circumferential surface of the outermost liner layer 140 may abut against the inner circumferential surface of the outermost braid-reinforced layer 125. The outer circumferential surface 120 of the outermost braid-reinforced layer 125 may form the outer circumferential surface of the tubular lead body 120.

In one embodiment, the liner layers 130 and 140 may be formed of polytetrafluoroethylene PTFE or another polymer material having similar properties. Each liner layer 130 and 140 may have a wall thickness of between approximately 0.001" and approximately 0.005". In one embodiment, the braid-reinforced layers 125 and 135 may each be formed of a conductor/fiber braid arrangement 115 (see FIGS. 3-10) imbedded in a wall material 162 of silicone rubber-polyurethane-copolymer ("SPC"), silicone rubber, polyurethane or another polymer material having similar properties. Each layer 125 and 135 may have a wall thickness of between approximately 0.004" and approximately 0.02".

In some embodiments, the layers 125 and 135 may both be braid-reinforced with the braid arrangement 115. However, in other embodiments, only one of the layers 125 and 135 may be braid-reinforced with the braid arrangement 115, the other non-braid-reinforced layer being simply a layer of SPC or other similar polymer material. For example, in one embodiment, the innermost layer 135 may be braid-reinforced with the braid arrangement 115 and the outermost layer 125 may not employ the braid arrangement 115. Conversely, in another embodiment, the outermost layer 125 may be braid-reinforced with the braid arrangement 115 and the innermost layer 135 may not employ the braid arrangement 115.

Figure 5:
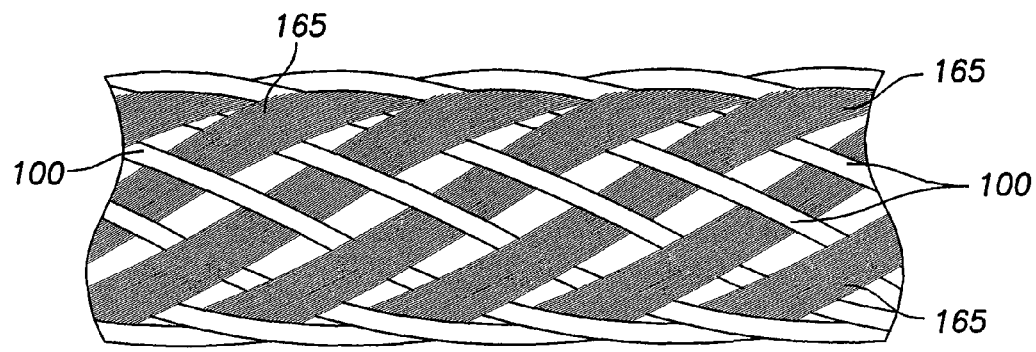
FIG. 5 is a side view of an example conductor/fiber braid arrangement that may be in at least one of the tubular layers or walls forming the tubular body of FIG. 3.
Figure 6:
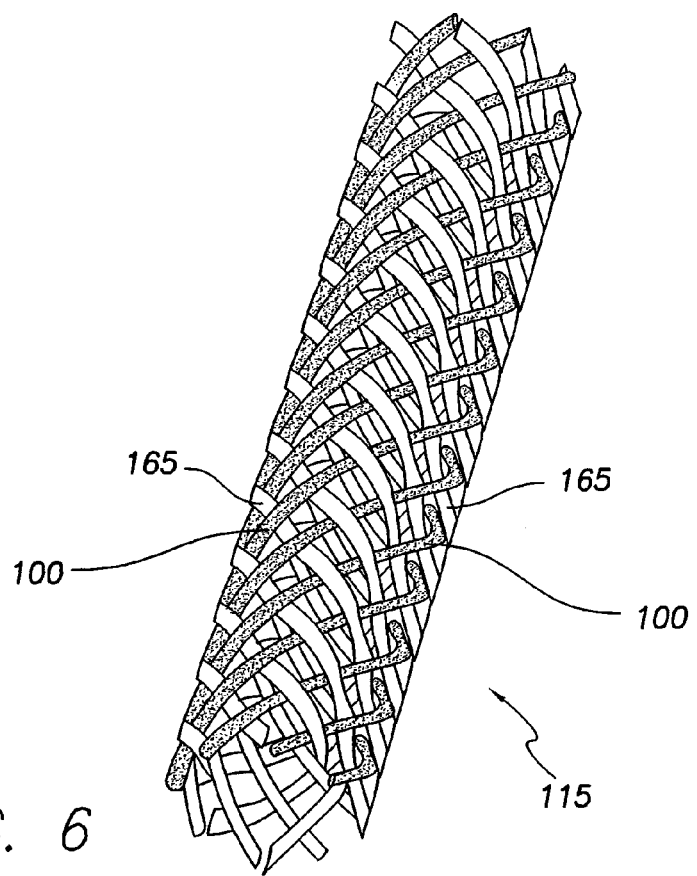
FIG. 6 is an isometric view of the conductor/fiber braid arrangement of FIG. 5.
Figure 7:
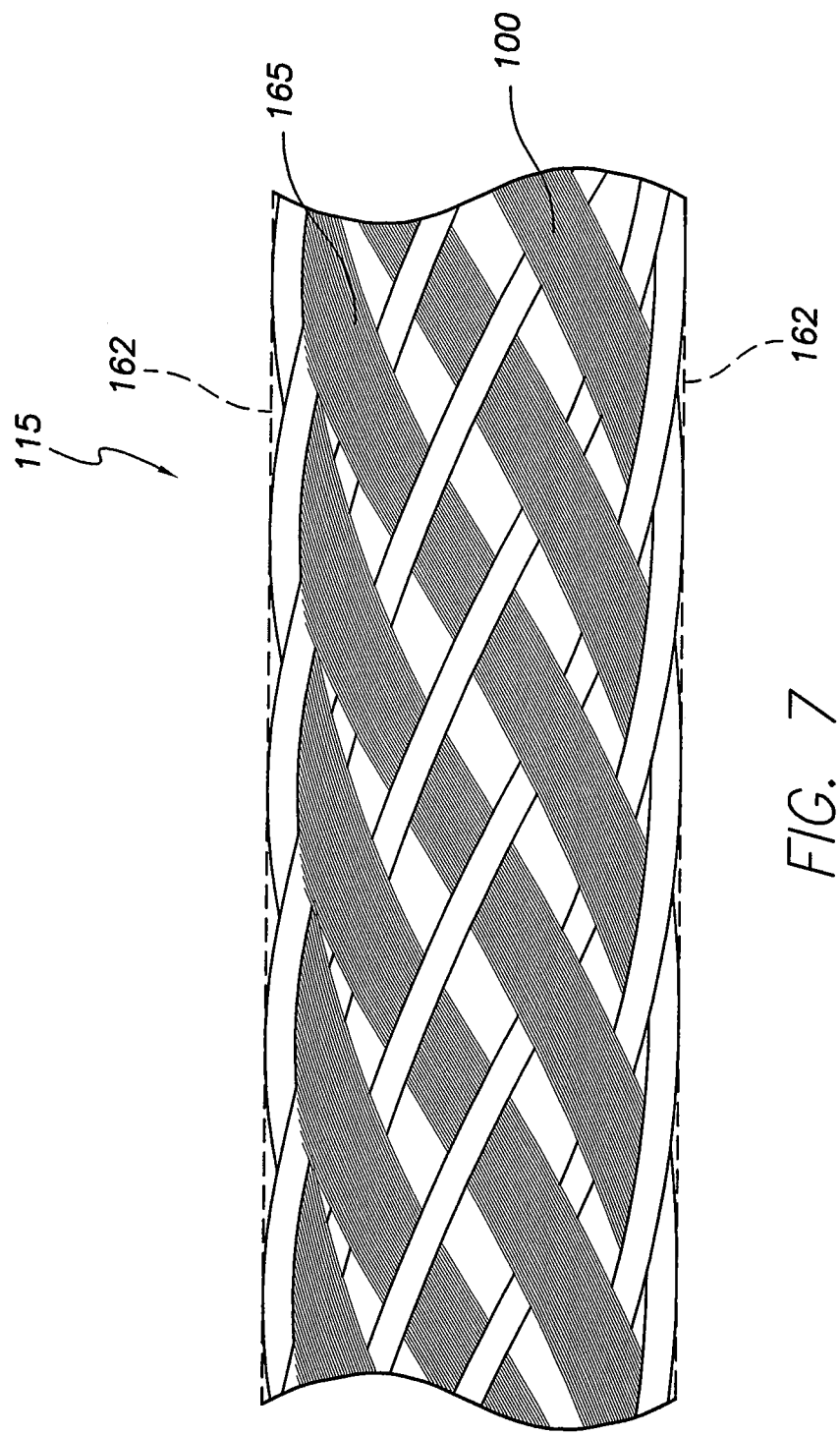
FIG. 7 is the same view as FIG. 5, except the conductor/fiber braid arrangement has been reflowed or molded with SPC to form a braided tubular wall or layer of the tubular body depicted in FIGS. 3 and 4.

For a discussion of an example braid arrangement 115, reference is now made to FIGS. 5 and 6. FIG. 5 is a side view of the example conductor/fiber braid arrangement 115 that may be in at least one of the tubular layers or walls 125 and 135 forming the tubular body 50 of FIG. 3. FIG. 6 is an isometric view of the conductor/fiber braid arrangement 115 of FIG. 5.

As can be understood from FIGS. 5 and 6, the braid arrangement 115 may be formed by braiding one, two or more single electrical conductors 100 with one, two or more ribbons 165. In one embodiment, a ribbon 165 may in the form of a fiberous polyester material. In other embodiments, a ribbon 165 may be in the form of a non-fiberous polymer material. In one embodiment, the ribbon 165 may be formed of polyester, nylon, KEVLAR™, expanded polytetrafluoroethylene ("ePTFE") or etc. The ribbon 165 may have a thickness of less than approximately 0.0005 inch.

As can be understood from FIGS. 5 and 6, the braid arrangement 115 may be wound in such a way that all the conductors 100 are spatially separated from each other via the ribbon 165 and form a helical coil pattern in the braid arrangement 115. The braid pattern as depicted in FIGS. 3, 5 and 6 may be such that each conductor 100, 105, 110 only crosses over ribbons 165 and not other conductors, and each ribbon 165 only crosses over the conductors, not other ribbons; thus, this braid pattern advantageously reduces the diameter of the braid arrangement 115 as compared to braid patterns where each conductor crosses over other conductors. The reduced diameter of the braid arrangement 115 disclosed herein saves space in the lead body 50.

Since the ribbon 165 acts as a spacer between the conductors 100, conductors 100 with or without individual electrical insulation jackets may be employed in the braid arrangement 115. As can be understood from FIG. 7, which is the same view as FIG. 5, except the conductor/fiber braid arrangement has been reflowed or molded (e.g., liquid injection mold ("LIM")) with SPC wall material 162 to form a braided tubular wall or layer 125 and 135 similar to those depicted in FIGS. 3, 4, 9 and 10.

As can be understood from FIGS. 3, 5 and 6, the braid pattern results in conductors 100, 105, 110 that are wound in an open pitch coil. Therefore, the conductors cannot touch each other and the resulting lead body 50 has improved balance with respect to stresses in the lead body, reducing the likelihood of waviness in the lead body surface subsequent to manufacture. The braid arrangement 115 acts as a structural member for the final lead body construction. The braid arrangement 115 imparts to the lead body 50 many improved mechanical characteristics, including improved torqueability, pushability, flex fatigue resistance, and kink resistance.

As can be understood from FIGS. 4-7, 9 and 10, in some embodiments, the braid arrangement 115 may have one or any multiple number of electrical conductors 100, and these conductors 100 may be routed singly through the braid arrangement 115. In other embodiments, as can be understood from FIGS. 3 and 4, the braid arrangement 115 may have one or any multiple number of electrical conductors 105 and 110, and these conductors 105 and 110 may be routed in pairs (as shown in FIGS. 3 and 4), in groups of three, groups of four, or etc. through the braid arrangement 115.

The configuration of the braid-reinforced layers 125 and 135 readily lends itself to the efficient coupling of the electrical conductors 105 and 110 to their respective electrodes 80 and 82. For example, as can be understood from FIG. 3 at arrow A, in one embodiment, the wall material 162 of the outer reinforced layer 125 may be removed via laser ablation, mechanical cutting or other methods to form a window 170 through the wall material 162 that exposes the appropriate conductors 110.

Figure 8:
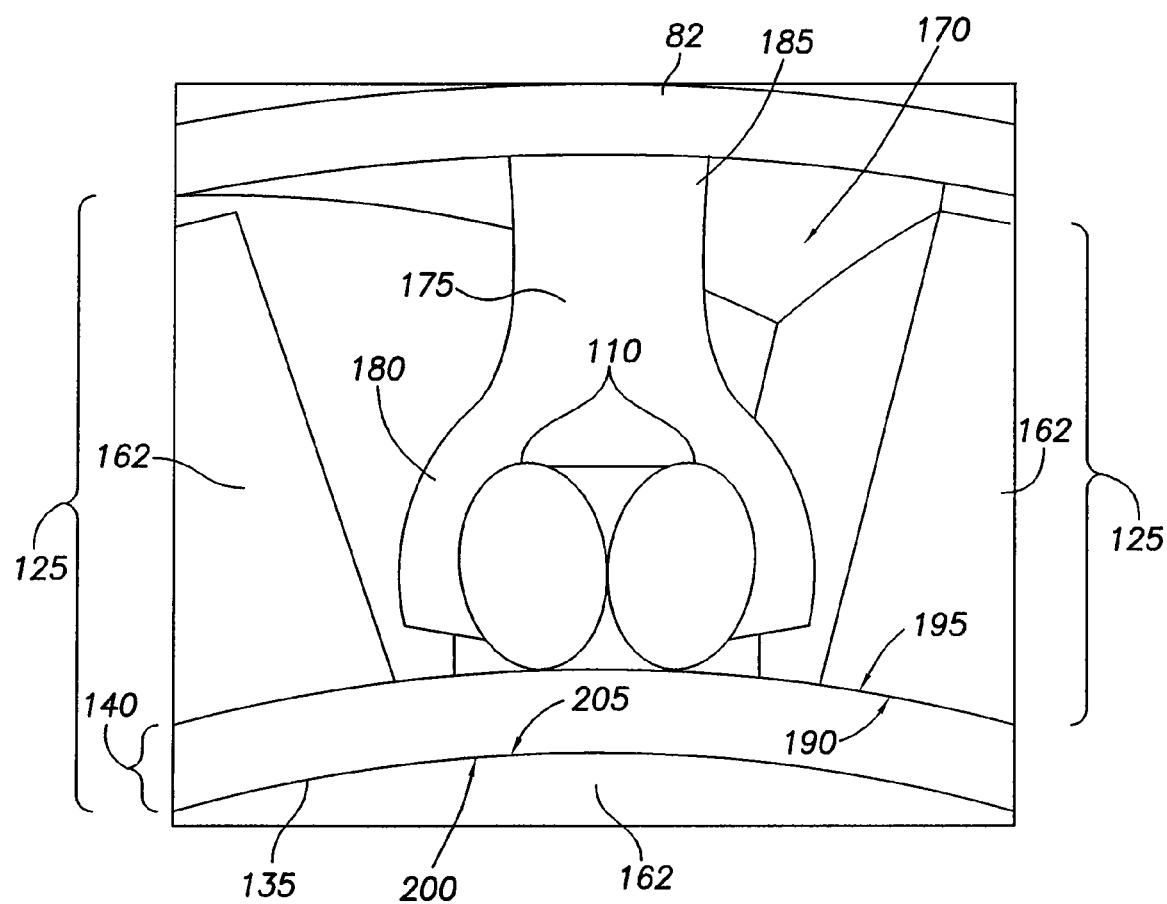
FIG. 8 is an enlarged partial transverse cross section through a window formed in the outer tubular wall or layer at arrow A and as taken along section line 8-8 in FIG. 3.

As can be understood from FIG. 8, which is an enlarged partial transverse cross section through the window 170 formed in the wall material 162 of the outer tubular wall or layer 125 at arrow A and as taken along section line 8-8 in FIG. 3, a crimp slug 175 may extend through the window 170 between an electrode (e.g., the shock coil 82 in this example) and the respective conductor pair 110. The bottom portion 180 of the crimp slug 175 may be crimped to the conductors 110 and the top portion 185 of the crimp slug 175 may be welded to the electrode 82.

As indicated in FIG. 8, the inner circumferential surface 190 of the outermost reinforced layer 125 abuts against the outer circumferential surface 195 of the outermost liner layer 140. As the outermost reinforced layer 125 may be assembled on the outermost liner layer 140, the two layers 125 and 140 may be considered to be a single outermost assembly layer 160. The inner circumferential surface 200 of the outermost liner layer 140 may displaceably abut against the outermost circumferential surface 205 of the innermost braid-reinforced layer 135 such that the innermost assembly layer 155 and outermost assembly layer 160 may coaxially displace relative to each other once assembled into the lead tubular body 50 and the outermost assembly layer 160 may be pulled over the innermost assembly layer 155 during the assembly of the lead tubular body 50.

Due to the innermost assembly layer 155 and outermost assembly layer 160 being coaxially rotatably relative to each other, in some embodiments, the innermost assembly layer 155 may serve in place of the helically coiled central conductor commonly found in active fixation leads and which are commonly used to extend/retract the helical active fixation anchors of such leads. The configuration of the innermost assembly layer 155 offers several advantages over the traditional helically coiled central conductor. For example, unlike the traditional helically coiled central conductor, the innermost assembly layer 155, due to its configuration/construction, offers a one-to-one torque transfer when used as the mechanism for extending/retracting the helical anchor 85.

Figure 9:
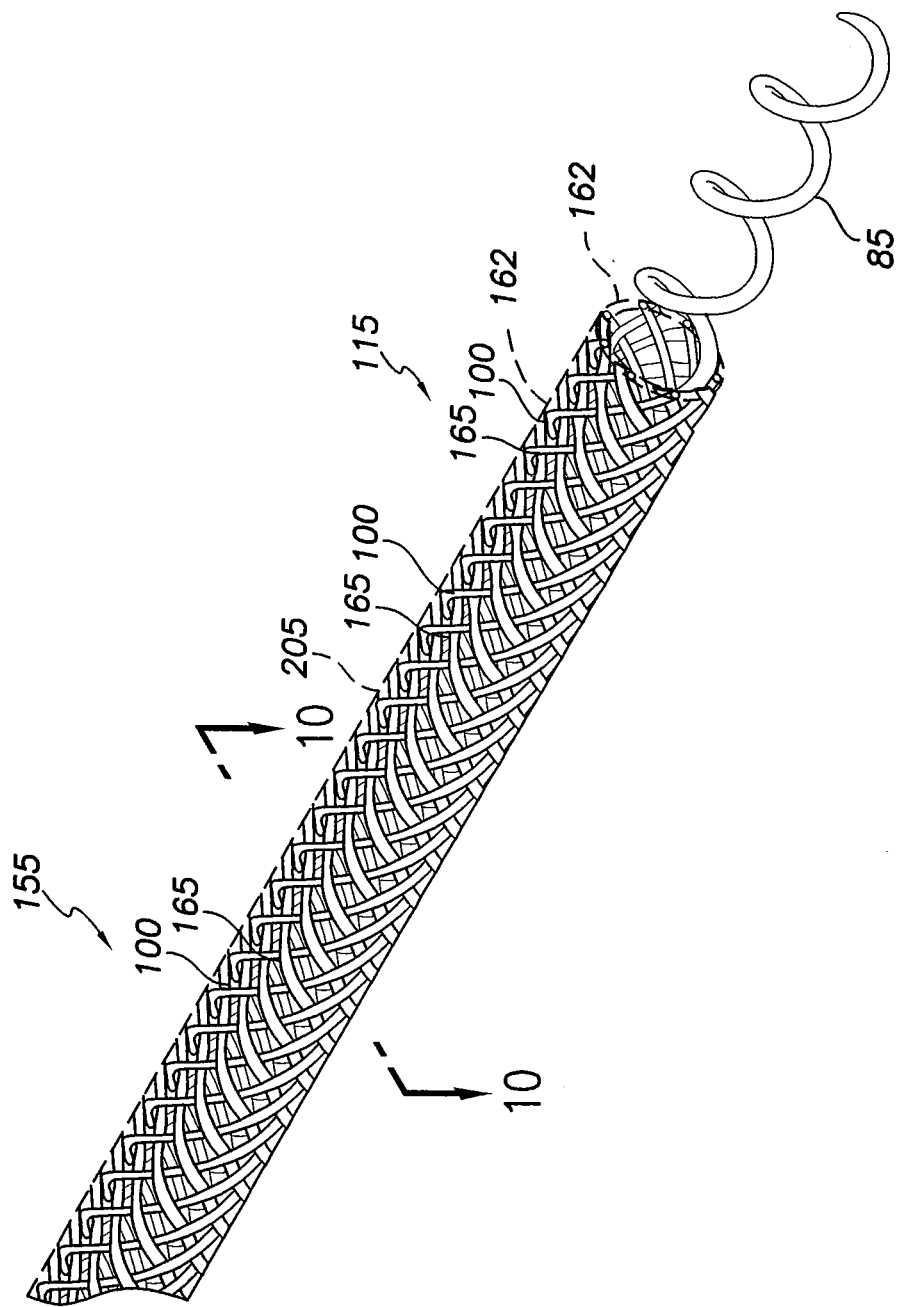
FIG. 9 is the same view of the tubular body of the medical lead depicted in FIG. 3, except depicting only the inner tubular wall or layer and helical anchor extending therefrom.
Figure 10:
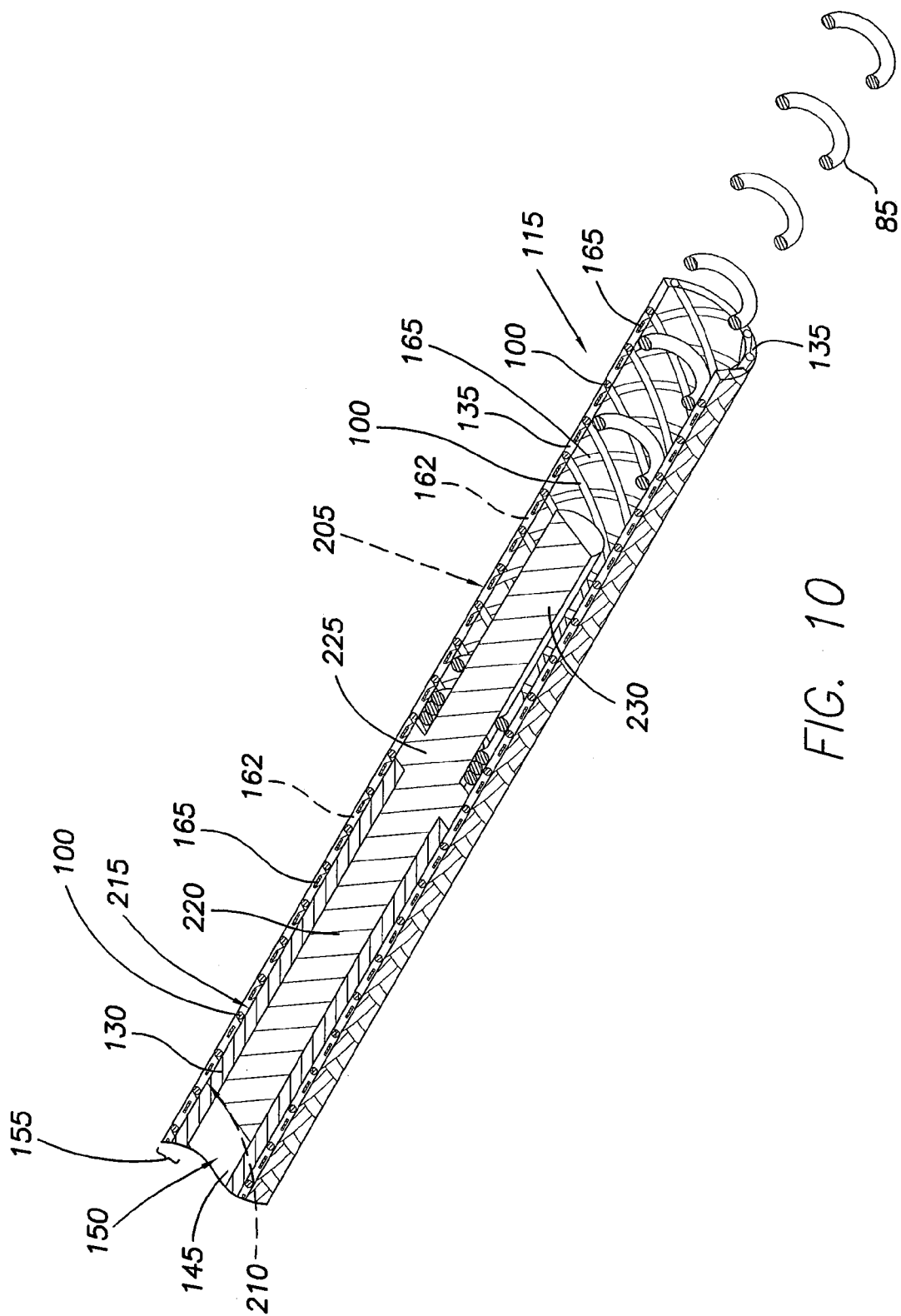
FIG. 10 is a longitudinal cross section of the inner tubular wall or layer as taken along section line 10-10 in FIG. 9.

A discussion of an embodiment of the lead tubular body 50 employing the innermost assembly layer 155 as the mechanism for rotatably extending/retracting the helical active fixation anchor 85 will now be given with respect to FIGS. 9 and 10. FIG. 9 is the same view of the tubular body 50 of the medical lead 10 depicted in FIG. 3, except depicting only the inner tubular wall or layer assembly 155 and helical anchor 85 extending therefrom. FIG. 10 is a longitudinal cross section of the inner tubular wall or layer assembly 155 as taken along section line 10-10 in FIG. 9. As shown in FIGS. 9 and 10, wherein the wall material 162 is shown in phantom line, the braid arrangement 115 may be generally identical to that depicted in FIGS. 5-7.

As can be understood from FIG. 10, the inner circumferential surface 210 of the innermost reinforced layer 135 abuts against the outer circumferential surface 215 of the innermost liner layer 130. As the innermost reinforced layer 135 may be assembled on the innermost liner layer 130, the two layers 135 and 130 may be considered to be a single innermost assembly layer 155. As discussed above, the outer circumferential surface 205 of the innermost braid-reinforced layer 135 may displaceably abut against the innermost circumferential surface 200 of the outermost liner layer 140 such that the innermost assembly layer 155 and outermost assembly layer 160 may coaxially displace relative to each other once assembled into the lead tubular body 50 and the outermost assembly layer 160 may be pulled over the innermost assembly layer 155 during the assembly of the lead tubular body 50.

As indicated in FIG. 10, a proximal end 220 of a metal helix shank 225 may be received within the distal end of the innermost liner layer 130 and coupled to the inner circumferential surface 155 of the layer 130. A distal end 230 of the shank 225 may be received within and coupled to the proximal end of the helical active fixation anchor 85. In a manner similar to that depicted in FIG. 8, the conductor 100 of the innermost reinforced layer 135 may be electrically coupled to the electrically conductive shank 225, which is electrically coupled to the helical anchor 85. Alternatively, in a manner similar to that depicted in FIG. 8, the conductor 100 may be electrically coupled to the proximal end of the helical anchor 85.

As can be understood FIGS. 3, 9, 10, and 11, which is the same view as depicted in FIG. 10, except showing both layer assemblies 155 and 160, because the helical anchor 85 is fixedly coupled to the distal end of the inner layer assembly 155 and the inner layer assembly 155 is capable of being displaced within the outer layer assembly 160, the helical anchor can be caused to extend/retract relative to the lead distal tip 70. More specifically, the extreme proximal end of the inner layer assembly 155 may be coupled to the pin contact 55 (see FIG. 1), which may be rotatable relative to the rest of the lead connector end 35 (see FIG. 1). Rotation of the pin contact 55 in a first direction may cause the inner layer assembly 155 to axially rotate within the outer layer assembly 160 and longitudinally displace within the outer layer assembly 160 such that the helical anchor 85 may be caused to extend distally from the opening 95 in the distal tip 70. Rotation in an opposite direction may cause the helical anchor 85 to retract back into the opening 95.

In one embodiment, the coupling of the shank 225 to the innermost liner layer 130 in combination with the configuration of the header assembly 235 (see FIG. 3) may be such that the helical anchor 85 is caused to extend/retract via rotation of the pin contact 55 despite the inner layer assembly 155 being limited to axial rotation relative to the outer layer assembly 160 and not being allowed to longitudinally displace within the outer layer assembly 160.

A variety of implantable medical leads 10 may be configured as described herein. For example, the lead 10 may be a cardiac lead (both high and low voltage), a multi-polar lead (both cardiac and neurologic), an MRI compatible lead, and an "intelligent" lead such as those intelligent leads that incorporate active components, such as sensors, integrated circuits, MEMS devices or drug delivery mechanisms.

The construction of a lead body 50 may be done on an individual basis or on a continuous basis. When the lead body 50 is manufactured on an individual basis, the conductors 100, 105, 110 and ribbon 165 may be braided together on a standard braiding machine to assemble the braid arrangement 115, which can then be stored on a spool until it is ready to be pulled as a whole or completed braid arrangement 115 onto a liner layer 130, 140 of the lead body 50 during the assembly process.

Prior to winding the braid assembly 115, the braid pattern, inside diameter and pitch may be determined according to the type of lead 10 being constructed, such as LV, high or low voltage. In some embodiments, the pitch may be varied at certain points along the length of the lead body 50 to impart different flexibility and torque characteristics at the certain points along the lead body 50.

Once the braid assembly 115 is braided, the braid assembly 115 may be stored on a large spool. When it is time to assemble a specific lead tubular body 50, the specific length of braid assembly 115 may be removed from the spool as needed for the specific length of the lead tubular body 50 being assembled. This specific length of braid assembly 115 may then be pulled over an innermost liner layer 130, which, as discussed above, may be PTFE or other applicable polymer materials. Once the braid assembly 115 extends about the outer circumferential surface 215 of the innermost liner layer 130, SPC (which is also known as OPTIM™ and will act as the wall material 162) may be reflowed or molded (e.g., LIM) about the braid assembly 115 and innermost liner layer 130 enclosed within the braid assembly 115. Specifically, in one embodiment employing reflowing, a SPC tube 162 may be pulled over the combined braid assembly 115 and liner layer 130. A fluorinated ethylene propylene ("FEP") jacket is then pulled over the SPC tube 162, the braid 115, and liner 130 and then subjected to reflow conditions to form the inner layer assembly 155. The FEP jacket is then removed from the resulting inner layer assembly 155.

In some embodiments, a mandrel is used to dip or extrude the PTFE liner 130 onto the mandrel outer circumferential surface. The PTFE innermost liner layer 130 is left on the mandrel as the braid 115 is braided over the outer circumferential surface 215 of the innermost liner layer 130. The SPC wall material 162 is then reflowed or molded over the PTFE liner layer 130 and braid 115, imbedding the braid 115 in the wall material 162. The mandrel can then be pulled from the completed assembly or left in the completed assembly for the addition of additional elements of the lead. The completed assembly can be stored on a spool in lengths of, for example, 500' or discrete lengths.

In multi-layer leads, the inner layer may be built as described above with respect to the mandrel process and stored on a spool or in discrete lengths, the mandrel for the inner layer being of a small diameter. A second or outer layer may then be assembled as described above with respect to the mandrel process, except the second mandrel is of a larger diameter as compared to the first mandrel. Once the second layer (i.e., outer layer) is completed, it may be pulled over the first layer (i.e., inner layer).

In some embodiments, the inner layer is assembled via any of the above described methods, and the outer layer assembly takes place by first pulling an outer PTFE layer over the assembled inner layer. The outer braid is then braided over the outer PTFE layer. The SPC wall material for the outer layer is then reflowed or molded over the outer braid and outer PTFE layer.

In one embodiment, the inner layer is a standard inner lead layer having, for example, a helical inner conductor coil surrounded by a PTFE liner. An outer layer with the imbedded braid, as described herein, could be pulled over the standard inner layer or assembled over the standard inner layer via any of the above-described methods.

At this point in the process, the conductor 100 may be laser ablated to expose the conductor 100 through the conductor insulation, if any, and the reflowed SPC wall material 162 to create a pathway that may be used to electrically couple the conductor 100 to the anchor electrode 85. A crimp slug may be applied to the exposed conductor 100 in preparation for electrically connecting the conductor 100 and electrode 85.

The shank 225 and its connected helical anchor electrode 85 may be inserted into the distal end of the inner layer assembly 155 and connected thereto. The crimp slug may then be laser welded to the helical anchor electrode 85 or the shank 225, which is electrically connected to the helical anchor electrode 85.

Generally speaking, a crimp slug may be attached to a conductor before or after the conductor insulation, if any, is removed. The form of a crimp slug may be open or closed, tubular or coiled, and/or circular. A conductor may be cut or left intact depending on the type of crimp slug used. This process may be repeated as many times as needed to attach the appropriate number of electrodes. Depending on where the electrode is located, the electrode may be a platinum band/ring, a half ring, a quarter ring, a coil, a helical active fixation anchor, and/or a sensor. The electrode may be attached to the crimp slug via laser welding.

After the electrode 85 has been attached to the crimp slug, any gaps around and under the electrode 85 are filled in with the appropriate material such as, OPTIM™, MedA, epoxy, etc. The proximal end of the conductor 100 and inner layer assembly 155 may then be coupled to respectively to the pin contact 55 and lead connector end 35.

Once the inner layer assembly 155 is completed, the construction of the outer layer assembly 160 may be begun. As with the inner layer assembly 155, the specific length of braid assembly 115 may be removed from the spool. This specific length of braid assembly 115 may then be pulled over an outermost liner layer 140, which, as discussed above, may be PTFE or other applicable polymer materials. Once the braid assembly 115 extends about the outer circumferential surface 195 of the outermost liner layer 140, SPC (which is also known as OPTIM™ and will act as the wall material 162) may be reflowed or molded (e.g., LIM) about the braid assembly 115 and outermost liner layer 140 enclosed within the braid assembly 115. Specifically, in one embodiment employing reflow, a SPC tube 162 may be pulled over the combined braid assembly 115 and liner layer 140. A FEP jacket is then pulled over the SPC tube 162, the braid 115, and liner 140 and then subjected to reflow conditions to form the outer layer assembly 160. The FEP jacket is then removed from the resulting outer layer assembly 160.

At this point in the process, the conductors 105, 110 may be laser ablated to expose the conductors 105, 110 through the conductor insulation, if any, and the reflowed SPC wall material 162 to create a pathway that may be used to electrically couple the conductors 105, 110 to the respective electrodes 80, 82. Crimp slugs may be applied to the exposed conductors 105, 110 in preparation for electrically connecting the conductors 105, 110 to their respective electrodes 80, 82.

As can be understood from FIGS. 3 and 8, where the lead employs a shock coil 82 and may be a high voltage lead, the conductive path to the shock coil 82 may include multiple conductors 110 that, when combined, meet the electrical requirements for shocking while the lead body 50 still offers a reduced diameter on account of the configuration of the braid assembly 115 employed in the outer layer assembly 160. Silicone, SPC or other materials may be added to the coil 82 to stabilize the coil 82 and create a non-tissue in-growth ("NTI") surface on the coil 82. The area adjacent the electrodes 80, 82 may be filled in with a reflowed or molded SPC or other material to create an isodiametric lead body 50.

In some embodiments, once the entire lead body is constructed via any of the above described methods, the entire lead body or portions thereof may be heat-set to assume a desired configuration that may, for example, allow passive fixation features to bias within a vein for LV implantation in the case of a CRT lead. Also, such heat-setting may be used for strain relief.

At this point, in one embodiment, the outer layer assembly 160 is pulled over the completed inner layer assembly 155 such that the outer circumferential surface 205 of the inner layer assembly 155 abuts against the inner circumferential surface 200 of the outer layer assembly 160. The crimp slugs of the respective conductors 105, 110 may then be laser welded to the respective electrodes 80, 82. After the electrodes 80, 82 have been attached to the crimp slugs, any gaps around and under the electrodes 80, 82 are filled in with the appropriate material such as, OPTIM™, MedA, epoxy, etc. The proximal end of the conductors 105, 110 and outer layer assembly 160 may then be coupled respectively to the ring contacts 60, 61 and lead connector end 35. In one embodiment, the resulting completed lead 10 may have a tubular body 50 with an braid-reinforced inner layer assembly 155 that is axially rotatable relative to an braid-reinforced outer layer assembly 160, thereby allowing the inner layer assembly 155 to be rotated via the pin contact 55 to cause the helical anchor electrode 85 to extend or retract at the lead distal end 70.

When the lead body 50 is manufactured on a continuous basis, the appropriate length of inner liner 130 may be selected depending on the type of lead 10 being constructed. The braid assembly 115 may then be braided over the outer circumferential surface 215 of the inner liner 130 in a continuous manner. If beneficial to the lead configuration and function, a variable pitch may be braided into the braid assembly 115 where desired during the braiding process. Once the braid assembly 115 is braided over the inner liner 130, the SPC wall material 162, crimp slugs, shank 225, anchor 85 and electrical connections may be completed as discussed above with respect to the individual basis discussion, thereby forming the inner layer assembly 155.

A braid assembly 115 is then braided onto the outer circumferential surface 195 of the outer liner layer 140. Once the braid assembly 115 is braided over the outer liner 140, the SPC wall material 162, crimp slugs, shank 225, anchor 85 and electrical connections may be completed as discussed above with respect to the individual basis discussion, thereby forming the outer layer assembly 160. The inner layer assembly 155 is then placed within the outer layer assembly 160 as discussed above with respect to the individual basis discussion, thereby forming the complete lead body 50. In one embodiment, the resulting lead body 50 has an inner braid-reinforced layer assembly 155 that is axially rotatable within an outer braid-reinforced layer assembly 160 to cause a helical anchor electrode 85 to extend/retract from the lead distal tip.

In some embodiments, the braid assembly 115 of the outer layer assembly 160 may be left exposed in certain selected discrete areas along the length of the lead body 50. These discrete areas of exposed braid assembly 115 may function as tissue in-growth locations where tissue may in-grow into the exposed braid assembly to facilitate chronic anchoring of the lead body 50 at the location of the implantation of the lead 10.

In some embodiments, one or more of the conductors 105 may instead be a tubular lumen extending distally from the lead proximal end. Such a lumen or lumens 105, although forming a portion of the braid assembly 115, may be used to transfer something other than current through the lead body 50. For example, such a lumen 105 of the braid assembly 115 may be used to deliver air, liquid, drugs, etc. from a proximal end of the lead to a location on the lead near the lead distal end.

In some embodiments, the helix anchor 85 at the lead distal end is not extendable/retractable relative to the lead distal end. Instead, the helix anchor 85 is fixed in an extended configuration and the entire lead body is rotated to imbedded the helix anchor 85 in cardiac tissue. Thus, in such fixed helix anchor embodiments, the inner layer of the lead body is not configured to rotate within the outer layer of the lead body or, alternatively, the lead body has a single layer.

The braid-reinforced layer assemblies 155, 160 used to form the lead tubular body 50 offer a number of advantages over known lead body configurations. For example, in some embodiments, the such braid-reinforced layer assemblies 155 may be substituted for helically wound central coils that are employed to extend/retract helical anchors; providing one-to-one torqueability, reduced manufacturing costs, and improved and more consistent flexibility as compared to leads employing the helically wound central coils known in the art.

The braid-reinforced layer assemblies 155, 160 allow greater flexibility in positioning an electrode along the lead body as the conductors of the assemblies 155, 160 are more readily located and accessible, as compared to lead configurations known in the art. As a result, the manufacturing of multi-electrode leads having, for example, 1-32 or more electrodes is made more feasible.

Since the conductors are imbedded in the material of the tubular wall, the French size made possible via the braid-reinforced layer assemblies 155, 160 may be substantially less than other leads commonly known in the art.

The leads disclosed herein are applicable to both cardiology applications and other medical areas, including neurological.

Figure 11:
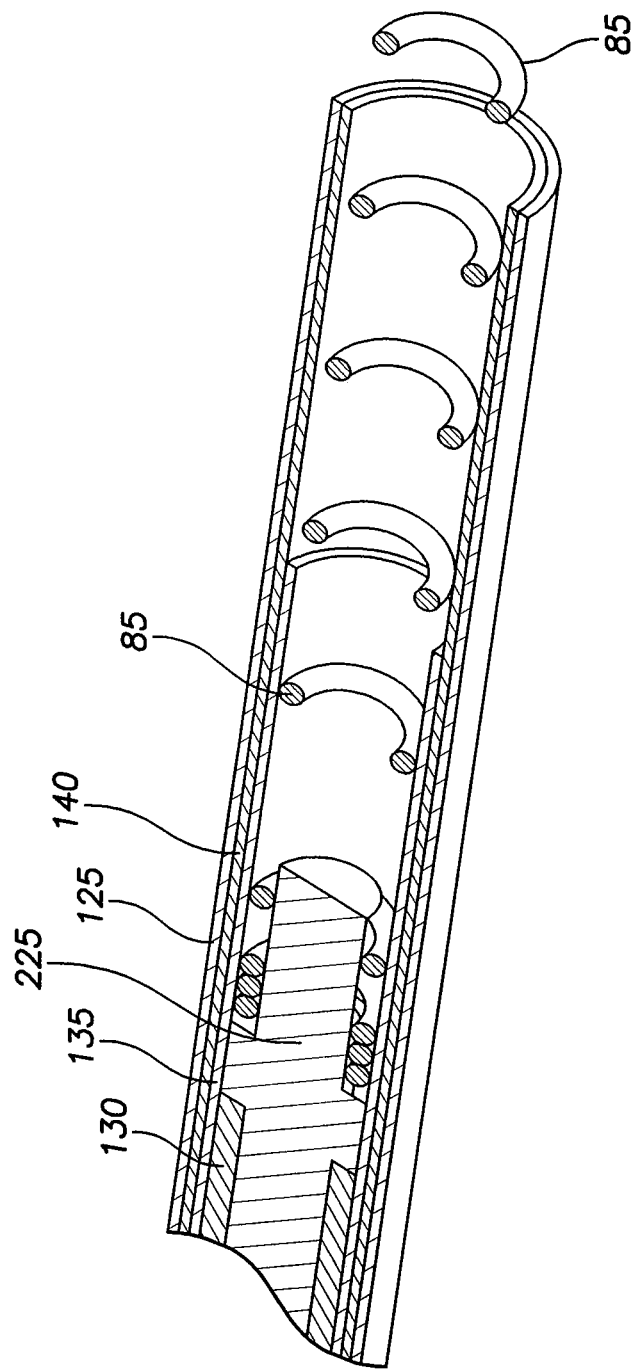
FIG. 11 is the same view as depicted in FIG. 10, except showing both layer assemblies.
Figure 11A:
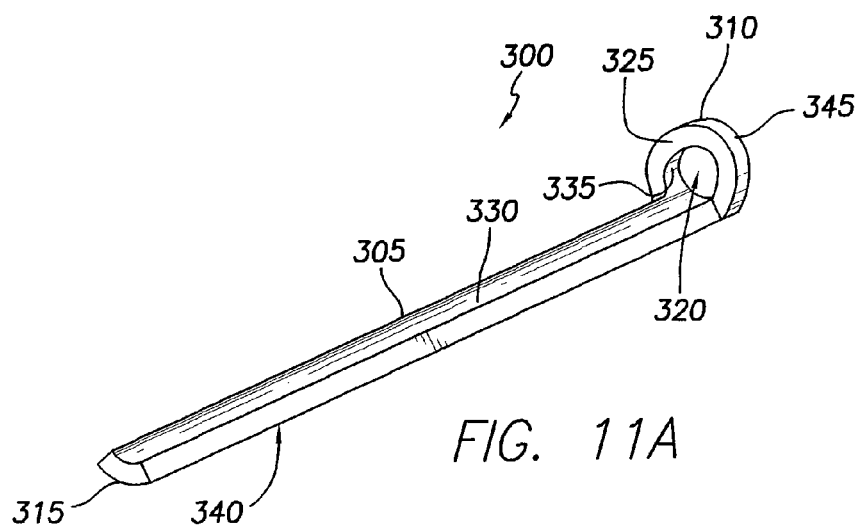
FIG. 11A is an isometric view of a zip tie type crimp slug.
Figure 11B:
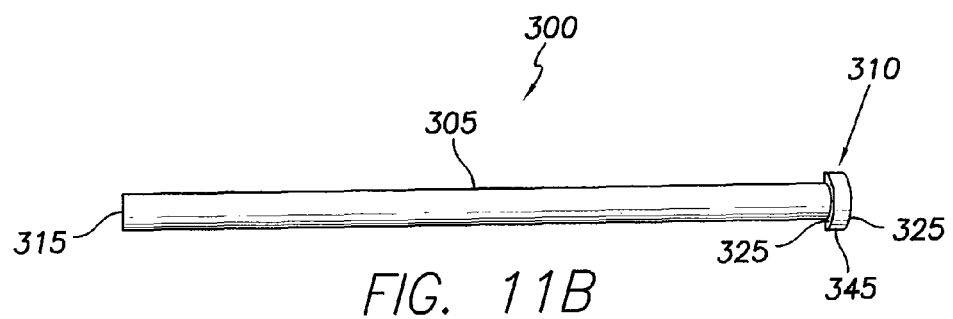
FIGS. 11B and 11C are, respectively, plan and side views of the crimp slug of FIG. 11A.
Figure 11C:
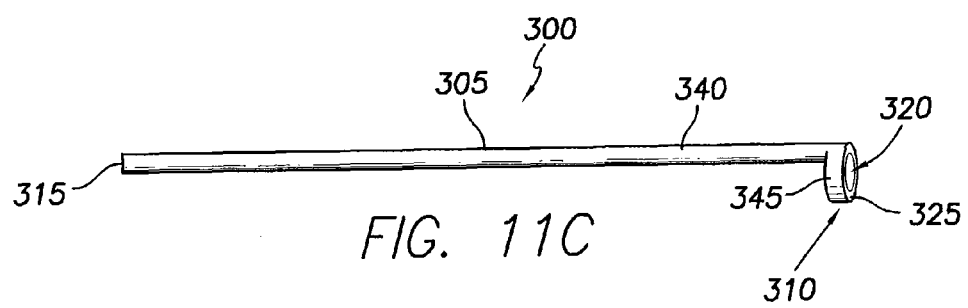

For a discussion regarding crimp slug configurations that can securely coupled to a variety of types of electrical conductors used in leads, including the helically wound conductors 100, 105, 110 of the above-described braided layers, reference is first made to FIGS. 11A-11C. FIG. 11A is an isometric view of a zip tie type crimp slug 300. FIGS. 11B and 11C are, respectively, plan and side views of the crimp slug 300 of FIG. 11A.

As shown in FIGS. 11A-11C, in one embodiment, the crimp slug 300 includes a ribbon or tail 305 and a collar 310. The tail 305 has a substantial length as compared to the size of the collar 310, extends from the collar 310 on one end, and terminates on the other end in the form of a tip or free end 315. The collar 310 includes a hole 320 defined therein and extends relative to the tail 305 such that the faces 325 of the collar 310 are generally transverse to the tail 310.

In one embodiment, the tail 305 includes an inner face 330 that is a generally flush extension of the arcuate inner surface 335 of the hole 320 and is similarly arcuate. The tail 305 includes an outer face 340 that is a generally flush extension of the arcuate outer surface 345 of the collar 310 and is similarly arcuate.

In one embodiment, the tail 305 extends between approximately 0.05" and approximately 0.5" from the adjacent collar face 325. The tail 305 has a transverse width of between approximately 0.005" and approximately 0.02". The tail 305 has a thickness of between approximately 0.001" and approximately 0.008". The collar 310 has an outer diameter of between approximately 0.01" and approximately 0.04". The collar 310 has a face to face thickness of between approximately 0.002" and approximately 0.01". The hole 320 has a diameter of between approximately 0.005" and approximately 0.02". The crimp slug 300 is formed of an electrically conductive material, such as, for example, platinum-iridium alloy, platinum, MP35N, or etc.

The crimp slug 300 depicted in FIGS. 11A-11C is advantageously configured such that it may be attached to a cable or a solid filament routed in either a wound or straight configuration. Even more advantageously, the crimp slug 300 can be coupled to such a cable or solid filament imbedded in a polymer (e.g., SPC) and only exposed in a specific region, as may be the case with conductors 100, 105, 110 of the embodiments of the lead body described above with respect to FIGS. 1-10.

Figure 12A:
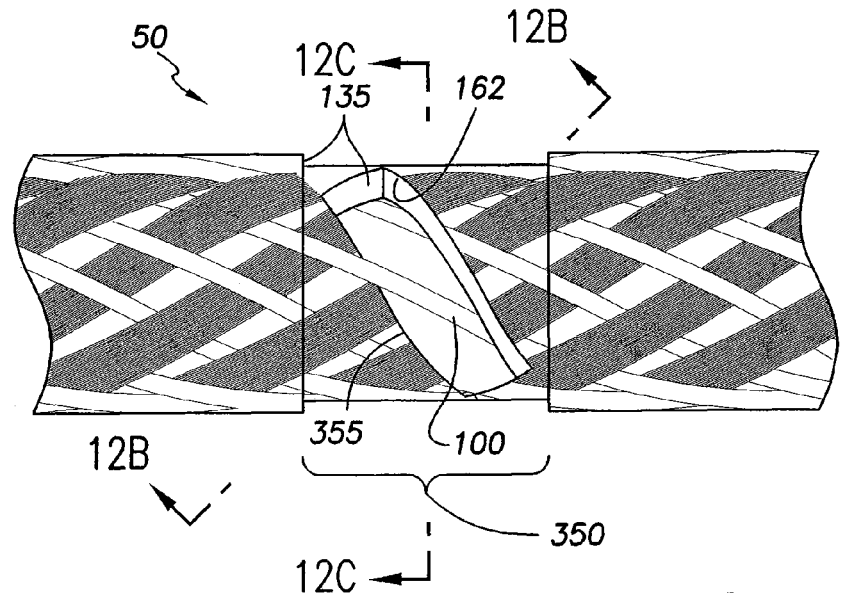
FIG. 12A is a plan view of a portion of a lead tubular body with a conductor helically routed about a liner layer and imbedded in the polymer material, the helically routed conductor and polymer material forming the reinforced layer.
Figure 12B:
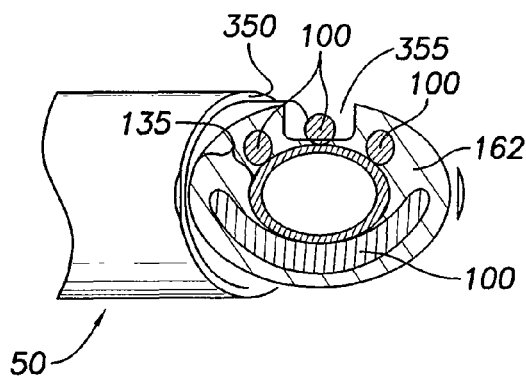
FIGS. 12B and 12C are, respectively, cross sections of the lead tubular body as taken along section line 12B-12B and section line 12C-12C in FIG. 12A.
Figure 12C:
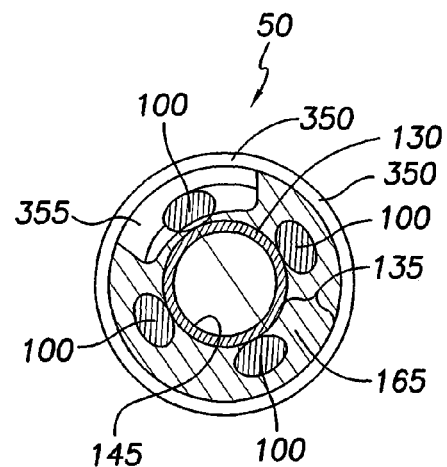

For a discussion of a method of preparing the lead body 50 for the coupling of the crimp slug 300 of FIGS. 11A-11C to a conductor 100 in the lead body, reference is made to FIGS. 12A-12C. FIG. 12A is a plan view of a portion of a lead tubular body 50 with a conductor 100 helically routed about a liner layer 130 and imbedded in the polymer material 162, the helically routed conductor 100 and polymer material 162 forming the reinforced layer 135. FIGS. 12B and 12C are, respectively, cross sections of the lead tubular body 50 as taken along section line 12B-12B and section line 12C-12C in FIG. 12A.

As shown in FIGS. 12A-12C, the polymer material 162 of the reinforced layer 135 is removed in the vicinity of a desired conductor access location to form a recessed ring 350 about the outer circumference of the tubular body 50 and a window 355 in the recessed ring 350 that extends in general alignment with the helically wound conductor 100 revealed by the window 355. The removal of the polymer material 162 may be accomplished via a variety of methods, including, for example, laser ablation. The ablation or other removal method may also be used to remove any electrical jacket that may be present about the conductor 100, thereby reveal the electrically conductive core of the conductor 100, as shown in FIGS. 12A-12C.

In one embodiment, the polymer material 162 may be masked during reflow to result in voids or openings that may be used to access the conductors or allow for the addition of conductive elements to the conductors.

Figure 13A:
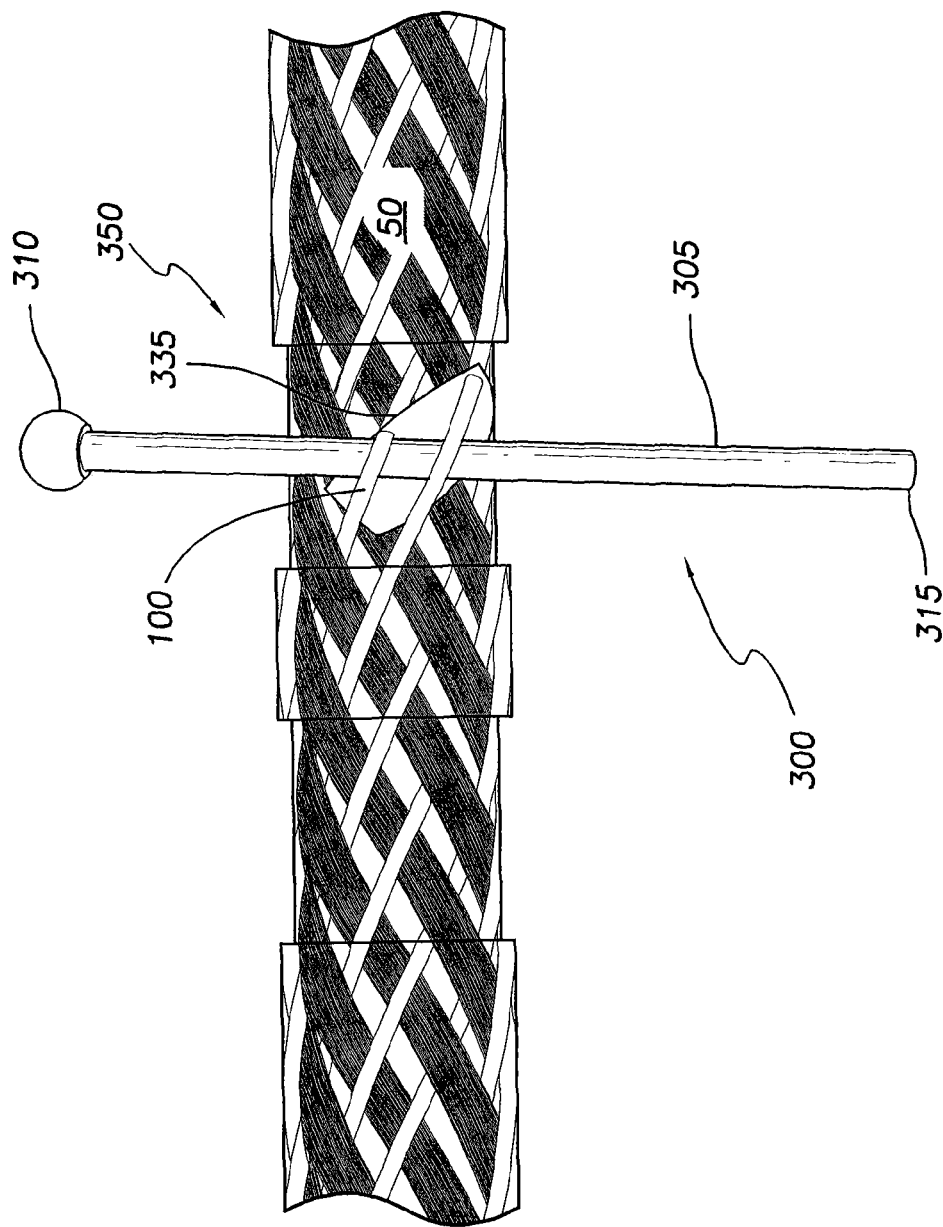
FIG. 13A is a view of the tubular body similar to the view depicted in FIG. 12A.
Figure 13B:
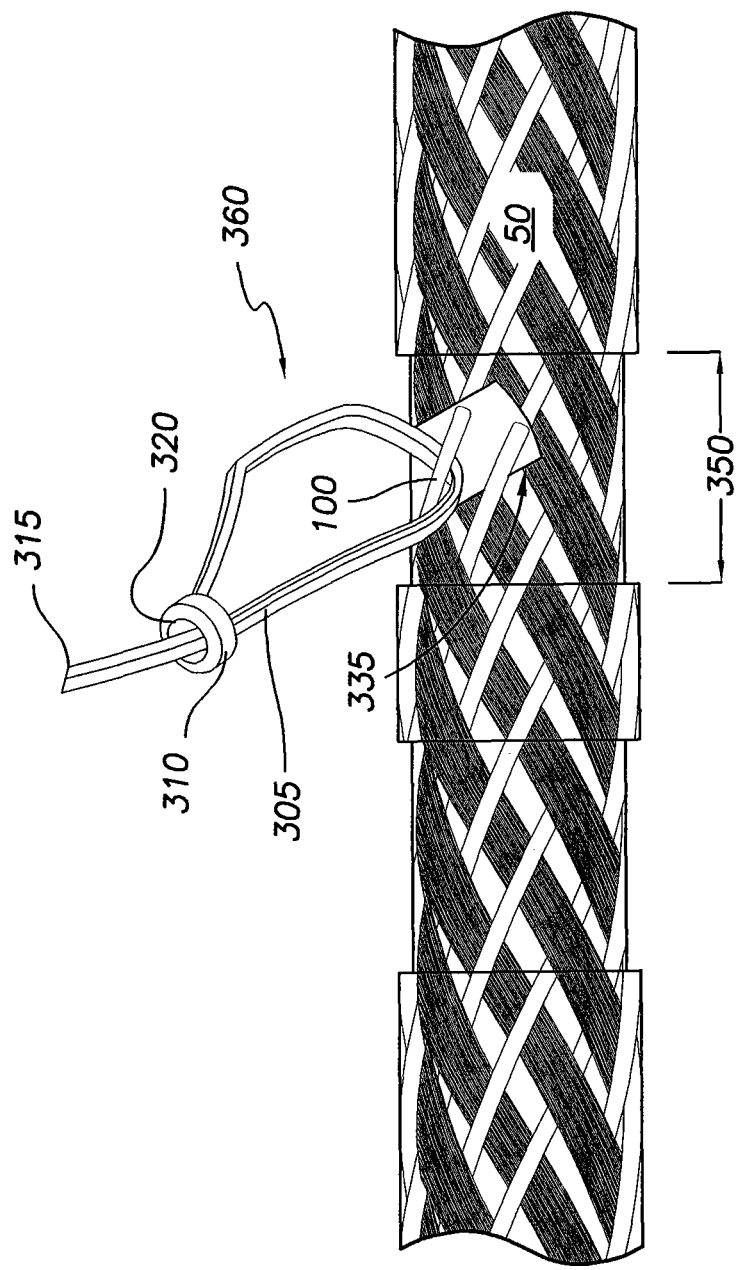
FIG. 13B is generally the same view of the tubular body depicted in FIG. 13A.
Figure 13C:
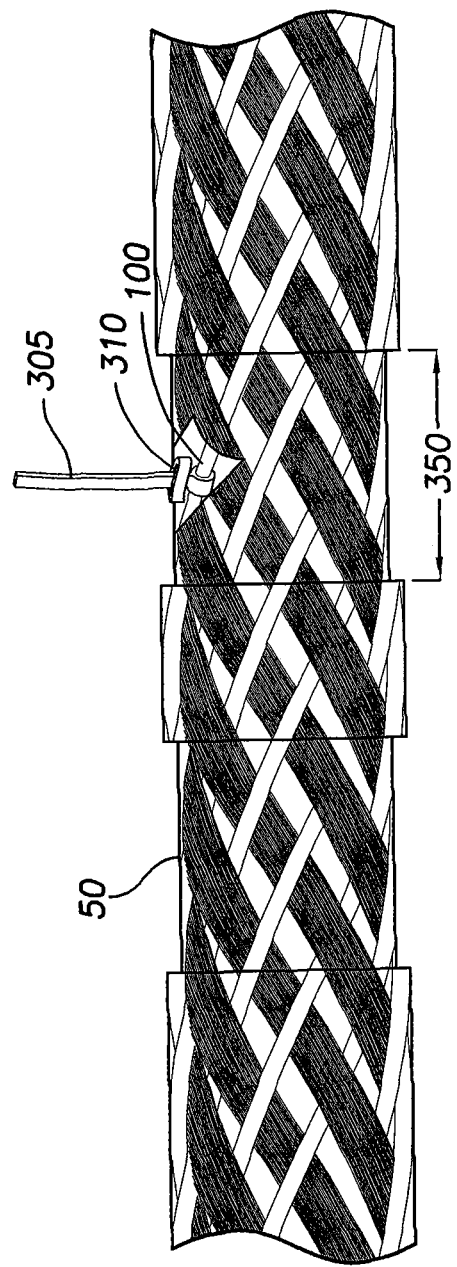
FIG. 13C is a side view of the lead body with the crimp fully cinched down on the conductor.
Figure 13D:
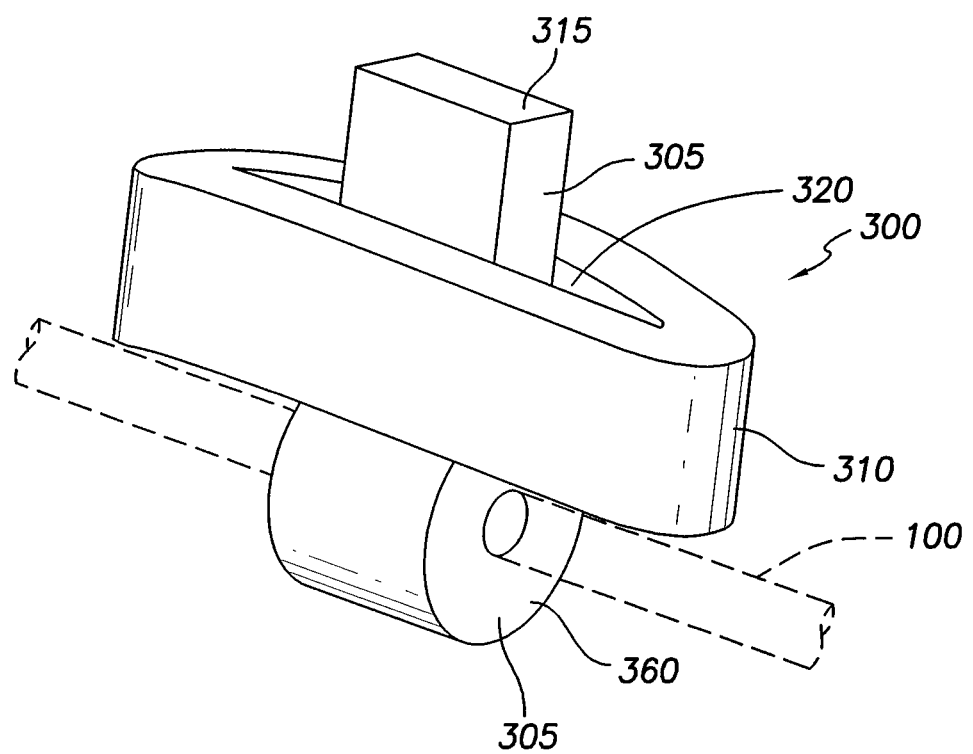
FIG. 13D is an isometric view of the crimp fully cinched down on the conductor, which is shown in phantom lines.
Figure 13E:
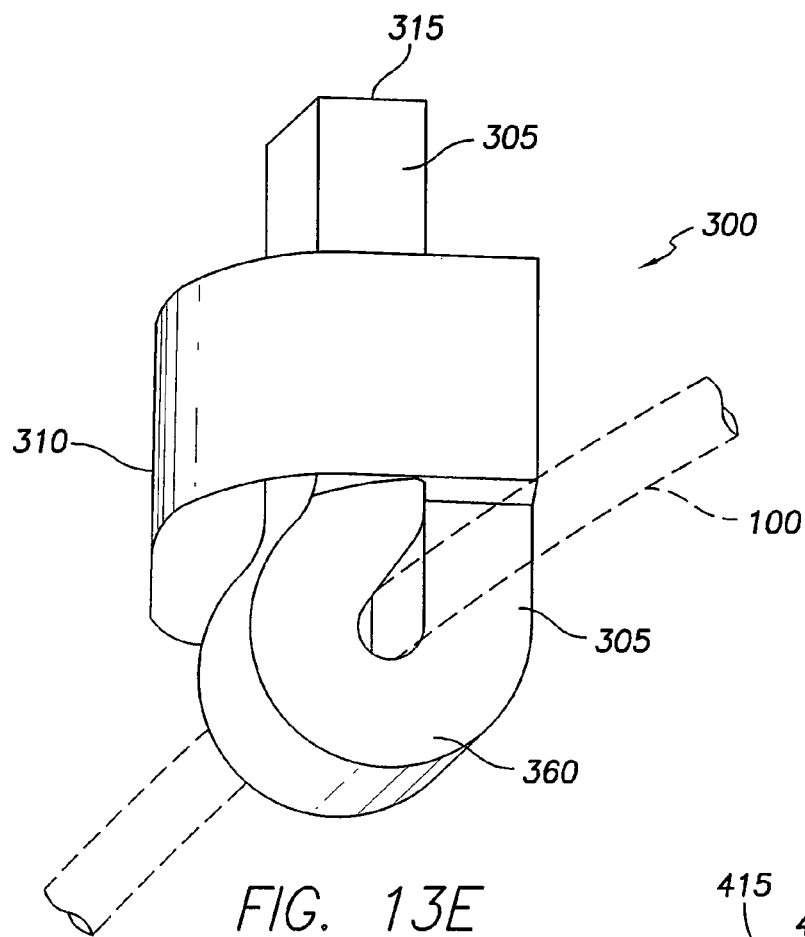
FIG. 13E is another isometric view of the crimp fully cinched down on the conductor, which is shown in phantom lines.

FIG. 13A is a view of the tubular body 50 similar to the view depicted in FIG. 12A and illustrating the beginning of the process of coupling the crimp slug 300 to the conductor 100 exposed in the window 355. Specifically, as shown in FIG. 13A, the tail 305 of the crimp 300 is inserted under the exposed conductor 100 by working the tip 315 of the crimp tail 305 under the conductor 100 and then further sliding the crimp tail 305 under the conductor 100 to cause the crimp collar 310 to move towards the conductor 100. As shown in FIG. 13B, which is generally the same view of the tubular body 50 depicted in FIG. 13A, the crimp tail tip 315, which is wrapped around the exposed conductor 100, is inserted through the crimp collar hole 320. The crimp 300 now forms a loop 360 about the exposed conductor 100. The crimp tail tip 315 is grasped (e.g., via a crimp tool) and pulled as the crimp collar 310 pushed down against the cable, cinching the crimp tail 305 down tight on the conductor 100. The crimp collar 310 can then be crimped down on the cinched tight tail 305 to hold the tail 305 tightly cinched about the conductor 100, as shown in FIG. 13C-13E. A final crimp of the collar may be applied to further lock the collar in position about the tightly cinched tail.

Figure 14A:
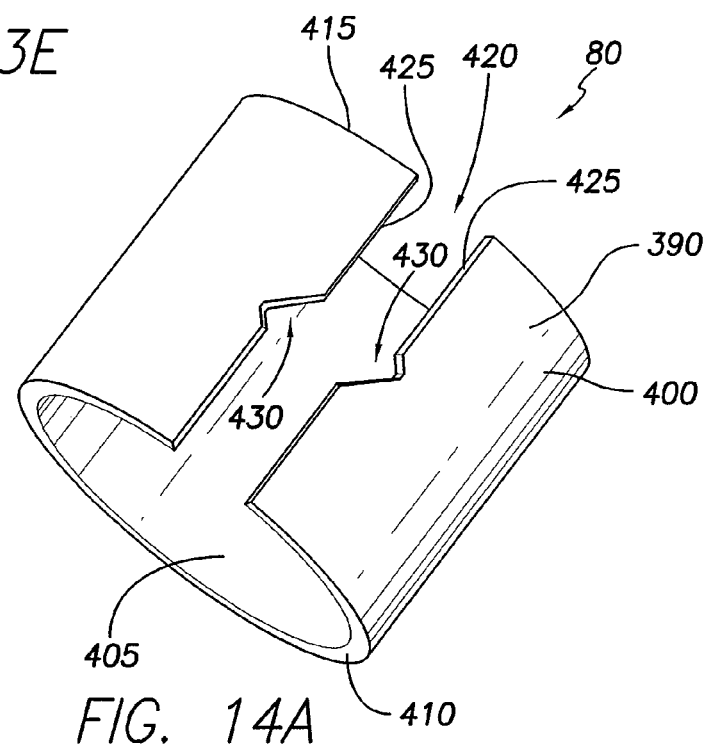
FIG. 14A is an isometric view of a split ring electrode in an expanded or split condition.

Once the crimp 300 is fully cinched down on the conductor 100 and fully crimped to lock the crimp 300 in place, a ring electrode 80 may be positioned on the lead body and coupled to the crimp 300. For example, as depicted in FIG. 14A, which is an isometric of a split ring electrode 80, an electrode 80 configured to be coupled to the crimp 300 may have an overall ring shape that includes a cylindrical wall 390 with an outer circumferential surface 400, an inner circumferential surface 405, an first end edge 410, a second end edge 415, and a slot, cut or split 420 extending through the wall 390 generally parallel to the axis of the electrode 80. The slot 420 is defined by opposed edges 425. Each opposed edge 425 includes a notch 430.

Figure 14B:
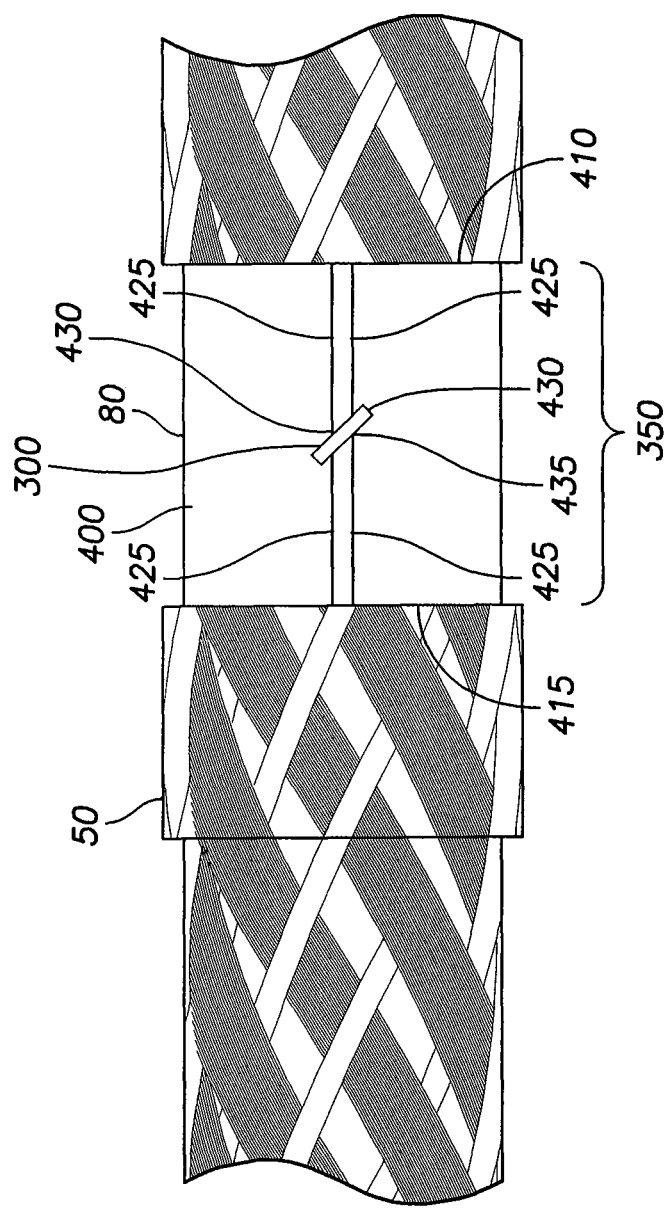
FIG. 14B is a view of a tubular body with the split ring electrode depicted in FIG. 14A in a non-expanded condition.

The ring electrode 80, when in an expanded or split condition as shown in FIG. 14A with the opposed edges 425 spaced apart from each other, has an inner diameter that is greater than the outer diameter of the lead body 50. Thus, when the ring electrode 80 is in the split condition shown in FIG. 14A, the lead tubular body 50 can be threaded through the ring electrode to cause the ring electrode to be positioned over the recessed ring 350 formed in the lead body (see FIG. 13C), the notches 430 being positioned on each side of the crimp 300. As shown in FIG. 14B, which is a view of the lead tubular body similar to that of FIG. 13B, the ring electrode 80 can then be transitioned to a contracted or non-split condition by pressing the opposed edges 425 of the ring electrode together such that the inner diameter of the ring electrode matches the outer diameter of the lead tubular body 50 at the recessed ring 350 and the outer diameter of the ring electrode 80 matches the outer diameter of the lead tubular body proximal and distal of the recessed ring 350. Thus, the ring electrode 80 in the non-split condition resides with the recessed ring 350 in the tubular body 50 and the outer circumferential surface 400 of the ring electrode 80 is generally flush with the outer circumferential surface of the lead body 50.

Figure 14C:
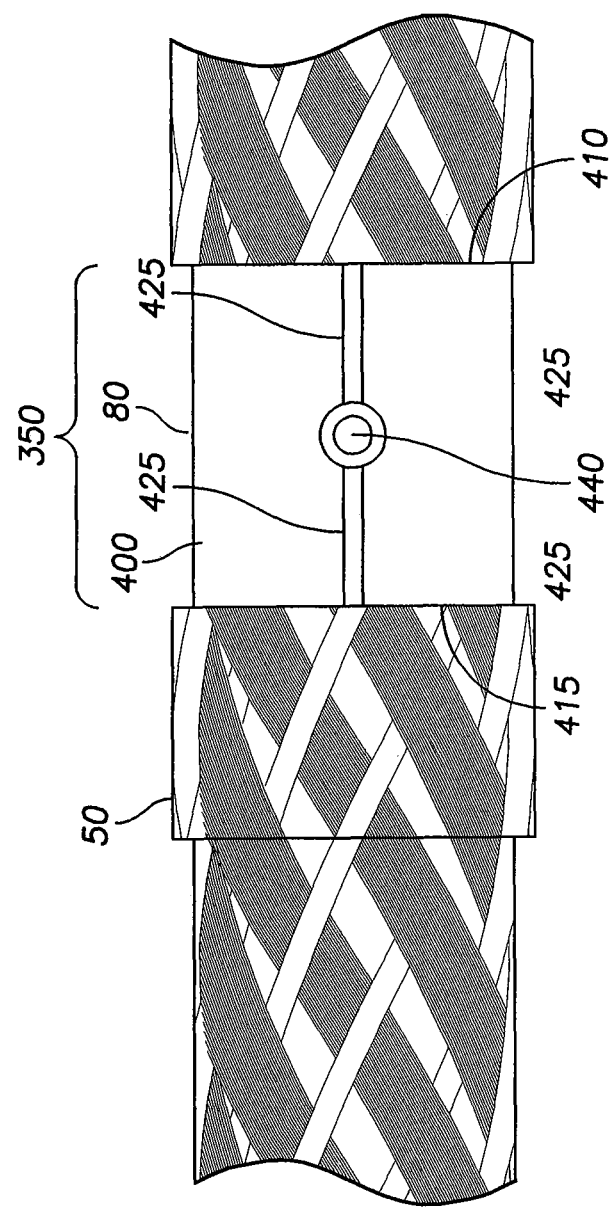
FIG. 14C is a view of the tubular body with a weld formed at a crimp of the split ring electrode depicted in FIG. 14A.

As indicated in FIG. 14B, when the ring electrode is positioned in the recessed ring 350 in a non-expanded condition with the opposed edges 425 abutting or nearly abutting each other and the crimp 300 is located between the notches 430, the notches 430 form a window or opening 435 in the wall of the ring electrode 80 through which the crimp 300 extends. As illustrated in FIG. 14C, a weld 440 can be formed at the location of the crimp and window to mechanically and electrically couple the crimp to the ring electrode and maintain the ring electrode in the non-expanded condition. Additional welds can be formed along the opposed edges 425 is it is desired to close off the seam formed by the opposed edges 425. It should be note that although in some embodiments the crimp 300 projects into the window 435, in other embodiments this may not be the case, the window simply serving for visualization during welding, the crimp simply being located below the window, but not projecting into the window.

The split ring electrode 80 of FIGS. 14A-14C combined with an ablated recessed ring in the lead body provides a novel way of creating an isodiametric lead body. While the split ring electrode works well with the ribbon type crimps discussed above, the split ring electrode can be used to attach to an assortment of more traditional crimps. The preferred configuration is to have a ribbon/post come through the split crimp window. However, the window can also just be used for visualization during welding, allowing the concept to be used in conjunction with almost any crimp currently used in the industry.

Figure 15A:
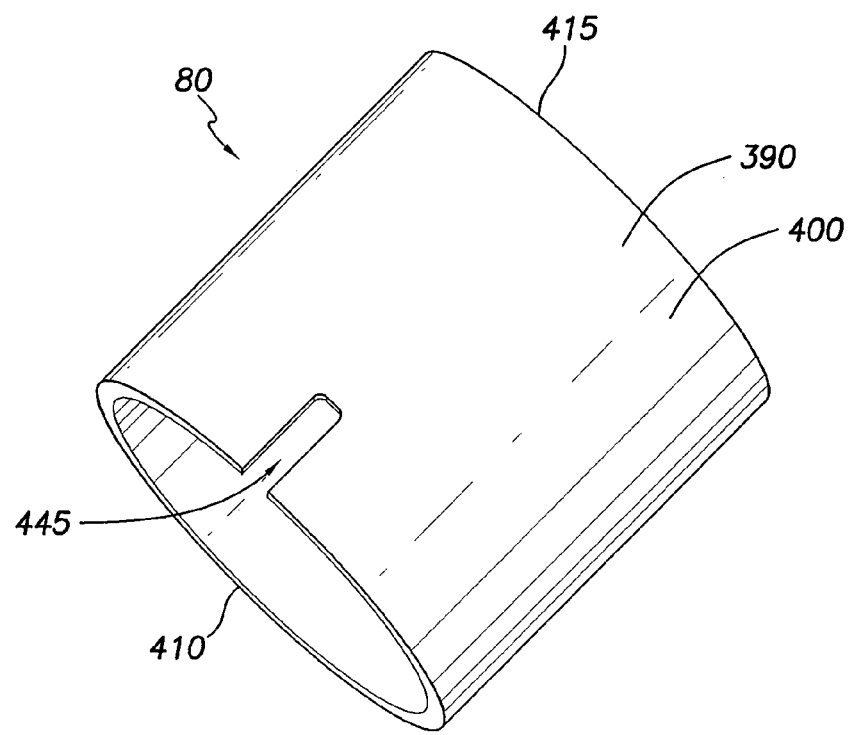
FIG. 15A is an isometric of a notched ring electrode.

Other ring electrode configurations may be employed with the crimp 300 For example, as depicted in FIG. 15A, which is an isometric of a notched ring electrode 80, an electrode 80 configured to be coupled to the crimp 300 may have an overall ring shape that includes a cylindrical wall 390 with an outer circumferential surface 400, an inner circumferential surface 405, an first end edge 410, a second end edge 415, and a notch 445 extending through the wall 390 oblique to the axis of the electrode 80. The notch 445 is defined in one of the end edges 410 and extend in the direction of the opposite edge for a portion of the length of the ring electrode.

Figure 15B:
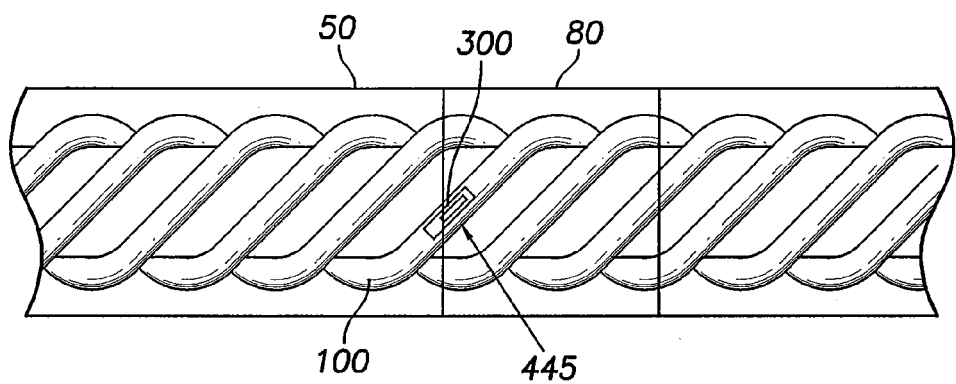
FIG. 15B is a view of the tubular body similar to that of FIG. 14B.

As shown in FIG. 15B, which is a view of the tubular body 50 similar to that of FIG. 14B, the ring electrode of FIG. 15A may be supported on the tubular body with the notch 445 positioned such that the crimp 300 is located within the notch 445. The notch 445 and crimp 300 can be welded together to form a weld similar to that discussed above with respect to FIG. 14C.

Figure 16A:
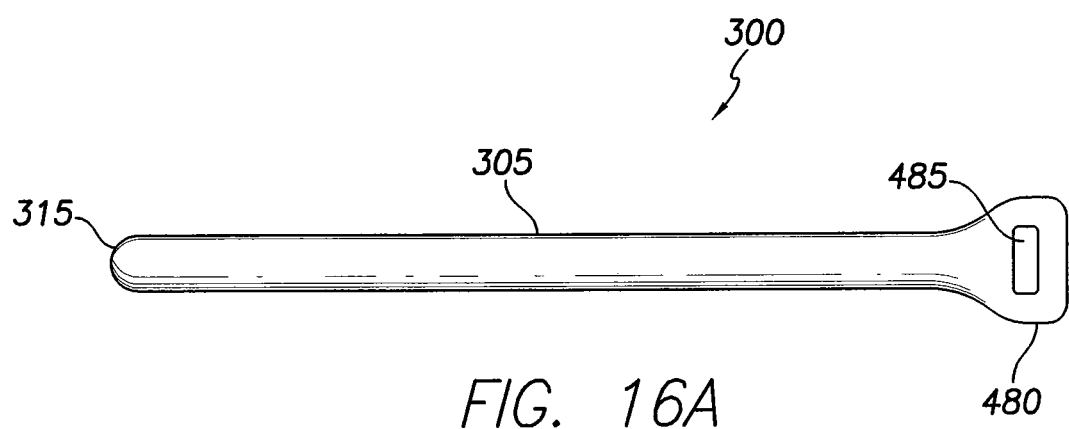
FIG. 16A is a plan view of another zip tie type crimp slug in a flat pattern condition.
Figure 16B:
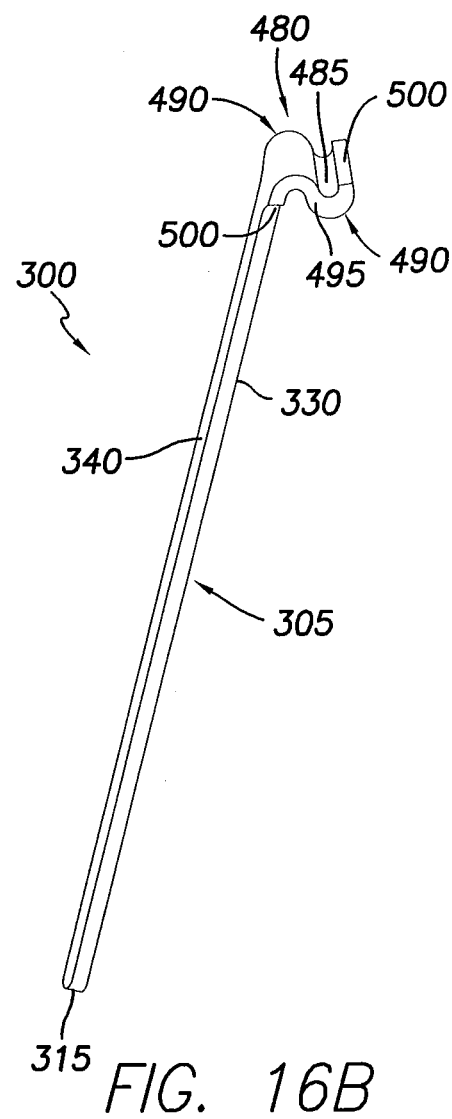
FIG. 16B is an isometric view of the zip tie type crimp slug of FIG. 16A in a formed state.
Figure 16C:
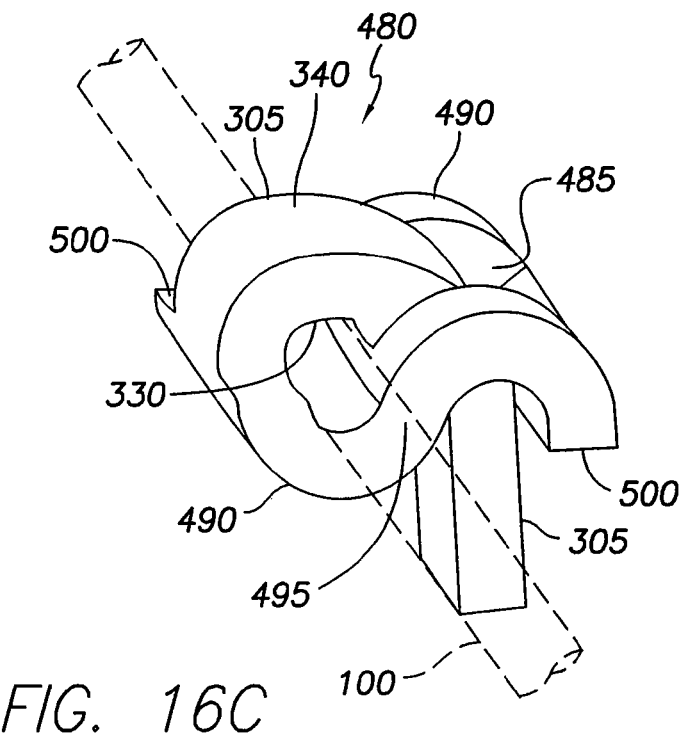
FIGS. 16C and 16D are, respectively, isometric and side views of the crimp slug of FIG. 16B in a looped condition.
Figure 16D:
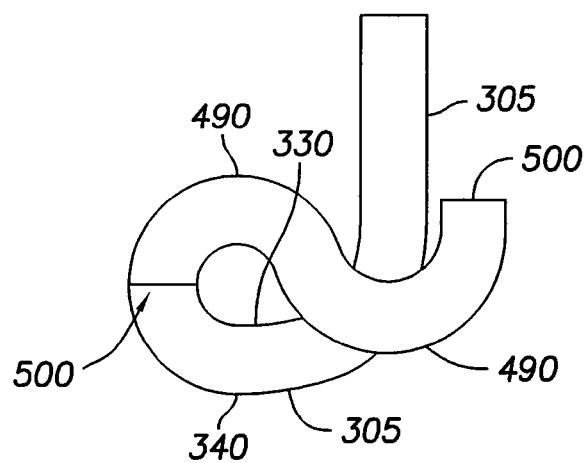

For a discussion regarding another crimp slug configuration, reference is now made to FIGS. 16A-16D. FIG. 16A is a plan view of another zip tie type crimp slug 300 in a flat pattern state. FIG. 16B is an isometric view of the zip tie type crimp slug 300 of FIG. 16A in a formed condition. FIGS. 16C and 16D are, respectively, isometric and side views of the crimp slug 300 of FIG. 16B in a looped state.

As shown in FIGS. 16A-16B, in one embodiment, the crimp slug 300 includes a ribbon or tail 305 and a slot head 480. The tail 305 has a substantial length as compared to the size of the slot head 480, extends from the slot head 480 on one end, and terminates on the other end in the form of a tip or free end 315. The slot head includes a slot 485 defined therein, the slot 485 extending transverse to the tail 310.

As shown in FIGS. 16B-16D, the slot head 480 includes two opposed half-cylinder portions 490, each half-cylinder portion 490 sharing a common longitudinal merged or joined wall portion 495 and each having a free longitudinal wall edge 500. The tail 305 extends from free wall edge 500 of one of the half-cylinder portions 490, and the slot 485 is defined in the center of the trough of the other half-cylinder portion 490. The slot 485 extends generally parallel to the longitudinal axis of the half-cylinder portion 490 in which the slot is defined. Since the half-cylinder portions 490 are opposed and share a common wall portion 495, the slot head 480 has a s-shaped side edges, as can be understood from FIGS. 16B-16D.

In one embodiment, the tail 305 includes an inner face 330 that is a generally flush extension of the arcuate inner surface of the trough of the half-cylindrical portion 490 from which the tail extends. The tail 305 includes an outer face 340 that is a generally flush extension of the arcuate outer surface of the half-cylindrical portion 490 from which the tail extends.

In one embodiment, the tail 305 extends between approximately 0.1" and approximately 0.5" from the free wall edge 500 from which the tail extends. The tail 305 has a transverse width of between approximately 0.005" and approximately 0.02". The tail 305 has a thickness of between approximately 0.002" and approximately 0.01". Each half-cylinder portion 490 has an outer diameter of between approximately 0.01" and approximately 0.04". Each half-cylinder portion 490 has an inner diameter of between approximately 0.003" and approximately 0.02". The slot head 480 has a length of between approximately 0.01" and approximately 0.1". The slot 485 has a width of between approximately 0.002" and approximately 0.012" and a length of between approximately 0.005" and approximately 0.025". The crimp slug 300 is formed of an electrically conductive material, such as, for example, platinum-iridium alloy, platinum, MP35N, or etc.

The crimp slug 300 depicted in FIGS. 16A-16D offers the same advantages of the crimp 300 depicted in FIGS. 11A-11C. Also, as can be understood from a comparison of the FIG. 16C to FIG. 13C, the crimp slug 300 of FIGS. 16A-16D may be secured to the conductor 100 and a ring electrode 80 in the same manner as the crimp slug 300 in FIGS. 11A-15B. Specifically, the tail 305 is looped around the conductor 100, threaded through the slot 485, and then cinched tight about the conductor 100. The slot head 480 is then crimped down on the tail to maintain the crimp slug 300 tightly cinched down on the conductor. The ring electrode can then be placed about the lead tubular body and welded to the crimp slug.

Figure 17A:
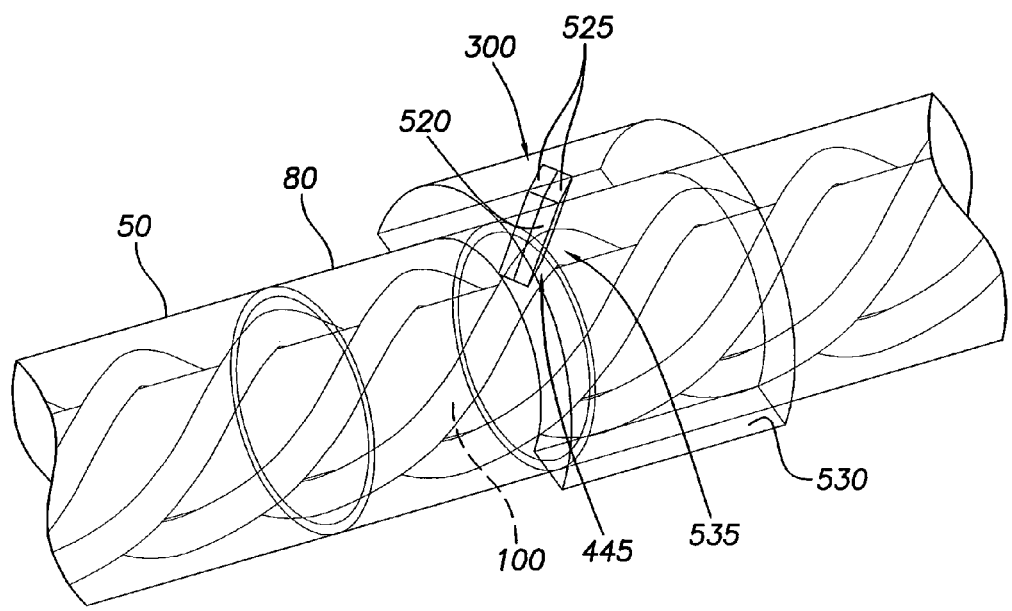
FIGS. 17A and 17B are, respectively, isometric and plan views of a lead body.
Figure 17B:
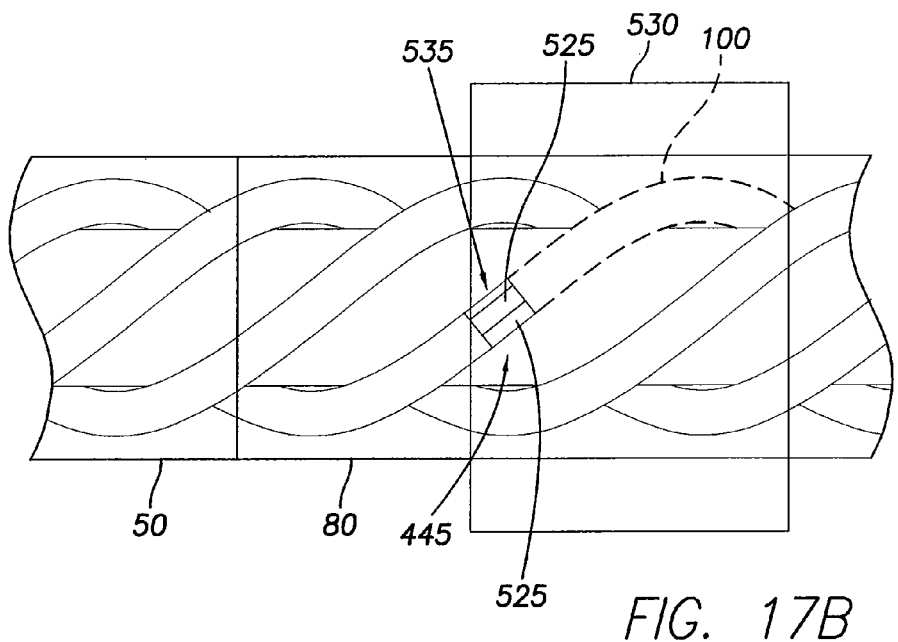

In one embodiment, as shown in FIGS. 17A and 17B, which are, respectively, isometric and plan views of a lead body, the crimp slug 300 is in the form of a ribbon or strip 520 that is inserted under the exposed conductor 100, the free ends 525 of the ribbon 520 being brought together and pulled such that the ribbon 520 is wrapped tightly about the exposed conductor 100. Specifically, the ribbon doubles back on itself and slides in to a slot 445 in the notched ring electrode 80 of FIG. 15A or a window 435 of the split ring electrode 80 of FIG. 14A. A half-cylinder shaped tool 535 having an arcuate inner surface that has diameter that generally matches the outer diameter of the lead body may be employed to crimp the ribbon about the conductor 100. The tool 535 may have a slot or notch 535 similar, but opposite to the slot or notch 445 in the ring electrode 80. Pulling on the ribbon free ends 525 and pushing with the tool 530 can cinch and crimp the ribbon 520 tightly down on the conductor 100. The ribbon can then be spot welded within the ring electrode notch 445.

The ribbon is formed of an electrically conductive material similar to that discussed above with respect to FIGS. 11A-11C and 16A-16D and may have dimensions similar to those discussed above with respect to the tail 305.

The embodiments of the crimp 300 discussed above with respect to FIGS. 11A-17B may be considered to have a tail portion (alternatively referred to as a ribbon portion) that can be slid under a conductor 100 imbedded in a layer of the lead body. These crimps can be constructed from a flat pattern or a tube and can take on many different configurations while still achieving the same general crimp concept. Also, any of these tail or ribbon equipped crimps 300 of FIGS. 11A-17B can be attached to two or more conductors 100 running next to each other (e.g., for the purposes of redundancy).

Figure 17C:
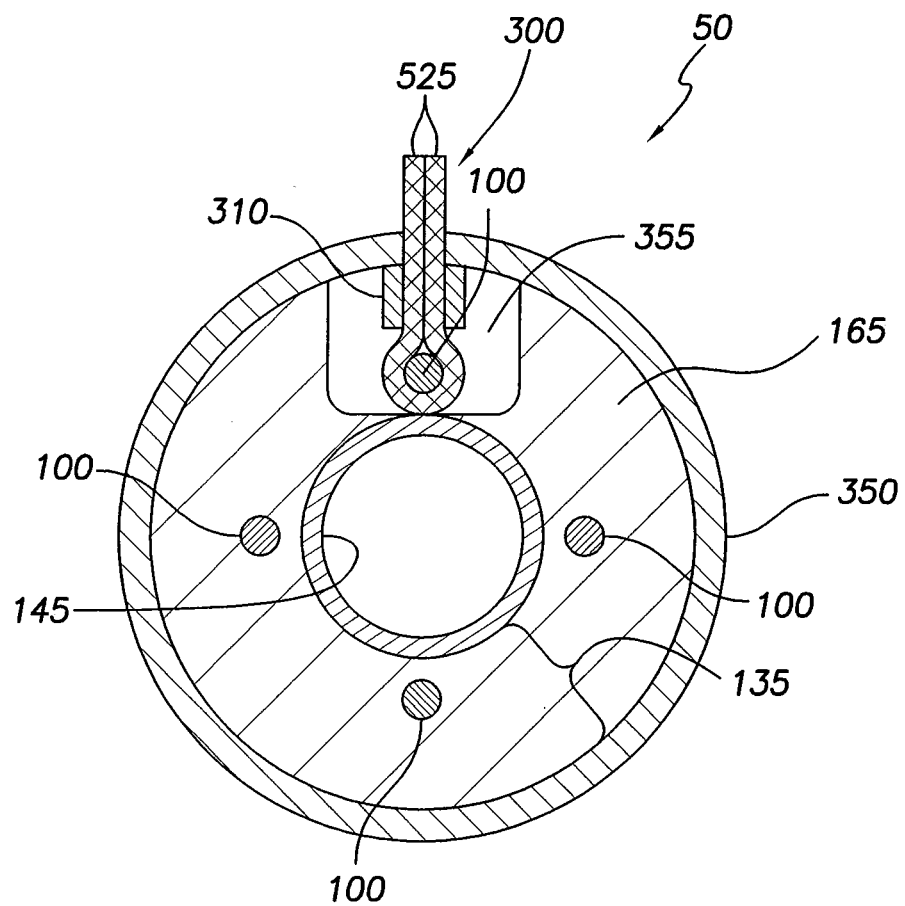
FIG. 17C is a transverse cross section of the lead body at a location of an alternative version of the ribbon equipped crimp of FIGS. 17A-17B.

In one embodiment, as depicted in FIG. 17C, which is a transverse cross section of the lead body 50 at a location of an alternative version of the ribbon equipped crimp 300 of FIGS. 17A-17B, the crimp 300 may include a collar 310 that is separate from the ribbon portion 525 of the crimp 300. Once the ribbon portion 525 is tightly wrapped about the conductor 100, the collar 310 can be slid down over the ribbon portion 525 and then crimped down on the ribbon portion 525. The ring electrode 350 can then be placed over the collar 310 such that the ribbon portion 525 extends from opening (e.g., slot) in the ring electrode and the collar 310 is in intimate contact with the inner surface of the ring electrode. The ribbon portion and collar can then be welded to the ring electrode.

The process of wrapping the ribbon portion around the conductor 100, cinching the crimp tight, and crimping, results in mechanically deformation between the crimp and the conductor. This ensures a reliable electrical and mechanical connection between the conductor and the crimp, which is then welded or otherwise mechanically and electrically coupled to the ring electrode.

These crimps 300 may be employed to couple conductors 100 to ring electrodes 80 that are in the form of split-ring electrodes, solid ring electrodes, half-ring electrodes, etc. These crimps 300 can also be used to couple the conductors 100 to shock coils 82 in the form of spot end or solid ring end shock coils. Finally, these crimps 300 can be used to coupled conductors 100 to additional features, such as, for example, sensors or chips.

These crimps 300 are particular useful when attaching to a straight or wound conductor 100 when the ends of the conductor are constrained or locked into a polymer matrix of a lead body. The ribbon equipped crimps 300 are particularly well suited for attachment to a wound conductor 100 because only a narrow ribbon 305 can be slid under the imbedded conductor 100. Also, the ribbon 305 facilitates the easy and secure coupling of the crimp to a helically routed conductor.

Figure 18A:
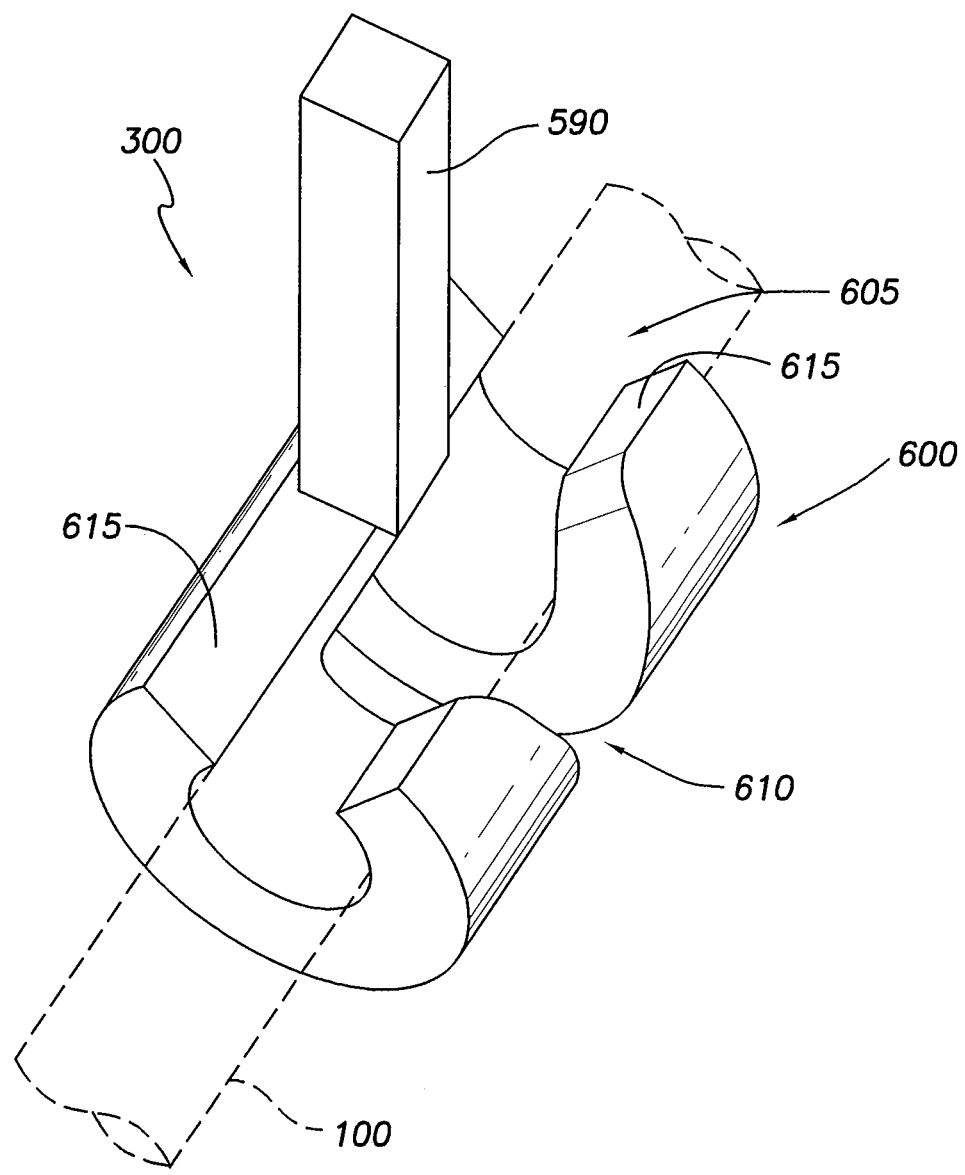
FIG. 18A is an isometric view of another embodiment of the crimp slug.

FIG. 18A is an isometric view of another embodiment of the crimp slug 30. As shown in FIG. 18A, the crimp 300 includes a tail 590 extending from a cylindrical head 600. The cylindrical head 600 includes a longitudinal slot 605 and a transverse slot 610. The longitudinal slot 605 is generally parallel to the longitudinal axis of the cylindrical head 600 and defines two longitudinal edges 615 in the wall of the head 600. The tail 590 extends from one of the edges 615, and the transverse slot 610 begins at the other edge 615. The tail 590 and transverse slot 610 are centered on the head 600 with respect to the length of the head.

As illustrated in FIG. 18A, the exposed conductor 100 is received in the trough of the cylindrical head 600. Specifically, the edge 615 in which the transverse slot 610 is defined is inserted under the exposed conductor 100 to cause the conductor to be received in the trough of the head 600.

Figure 18B:
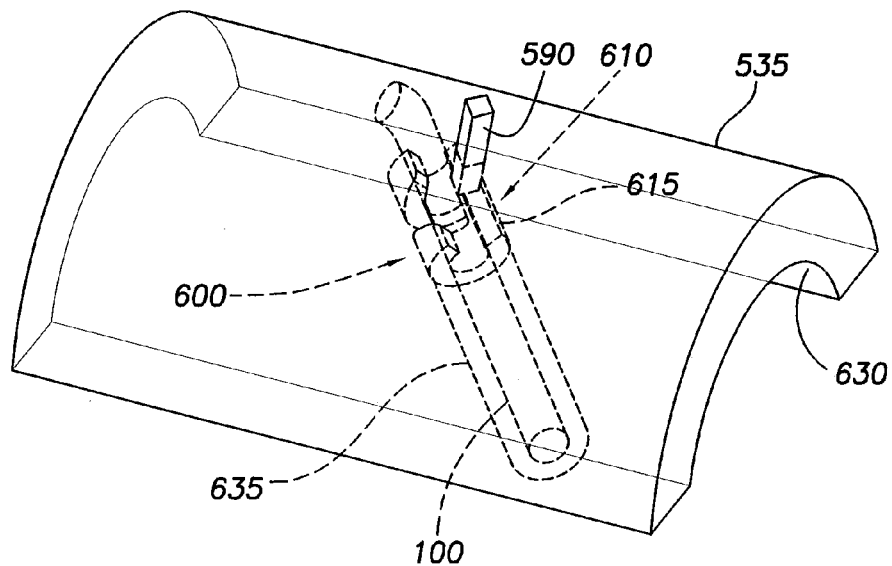
FIGS. 18B and 18C are, respectively, top and bottom isometric views of a half-cylinder shaped tool for use in crimping the crimp on an exposed conductor.
Figure 18C:
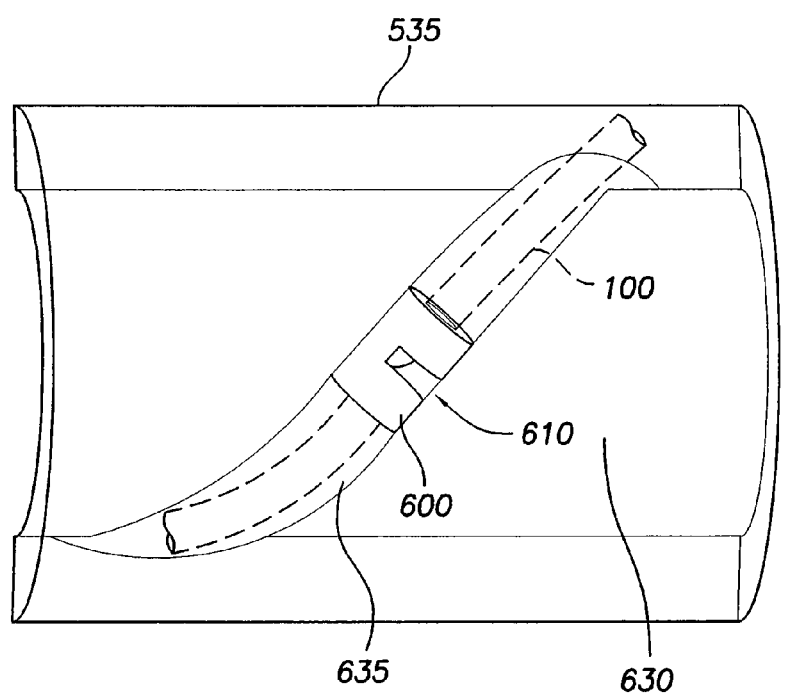

As indicated in FIGS. 18B and 18C, which are, respectively, top and bottom isometric views of a half-cylinder shaped tool 535 for use in crimping the crimp 300 on an exposed conductor 100, the tool 535 has an arcuate inner surface 630 that has diameter that generally matches the outer diameter of the lead body. A helically routed groove or recess 635 is defined in the arcuate inner surface 630. An opening 640 extends through the wall 645 of the tool 535 from the recess 635. The tail 590 of the crimp 300 extends through the opening 640 when the cylindrical head 600 of the crimp 300 is received in the opening 640.

Pulling on the tail and pushing with the tool 530 can cinch and crimp the ribbon cylindrical head 600 tightly down on the conductor 100. The tail 590 can then be spot welded within the ring electrode notch 445 or window 435.

In one embodiment, the tail 590 extends between approximately 0.01" and approximately 0.2" from the edge 615 from which the tail extends. The tail 590 has a transverse width of between approximately 0.002" and approximately 0.02". The tail 590 has a thickness of between approximately 0.002" and approximately 0.01". The cylinder head 600 has an outer diameter of between approximately 0.012" and approximately 0.03". The cylinder head 600 has an inner diameter of between approximately 0.004" and approximately 0.015". The cylinder head 600 has a length of between approximately 0.02" and approximately 0.1". The longitudinal slot 605 has a width of between approximately 0.003" and approximately 0.02" and a length of between approximately 0.02" and approximately 0.1". The transverse slot 610 has a width of between approximately 0.003" and approximately 0.022" and a length of between approximately 0.01" and approximately 0.04". The crimp slug 300 is formed of an electrically conductive material, such as, for example, platinum-iridium alloy, platinum, MP35N, or etc.

Figure 19:
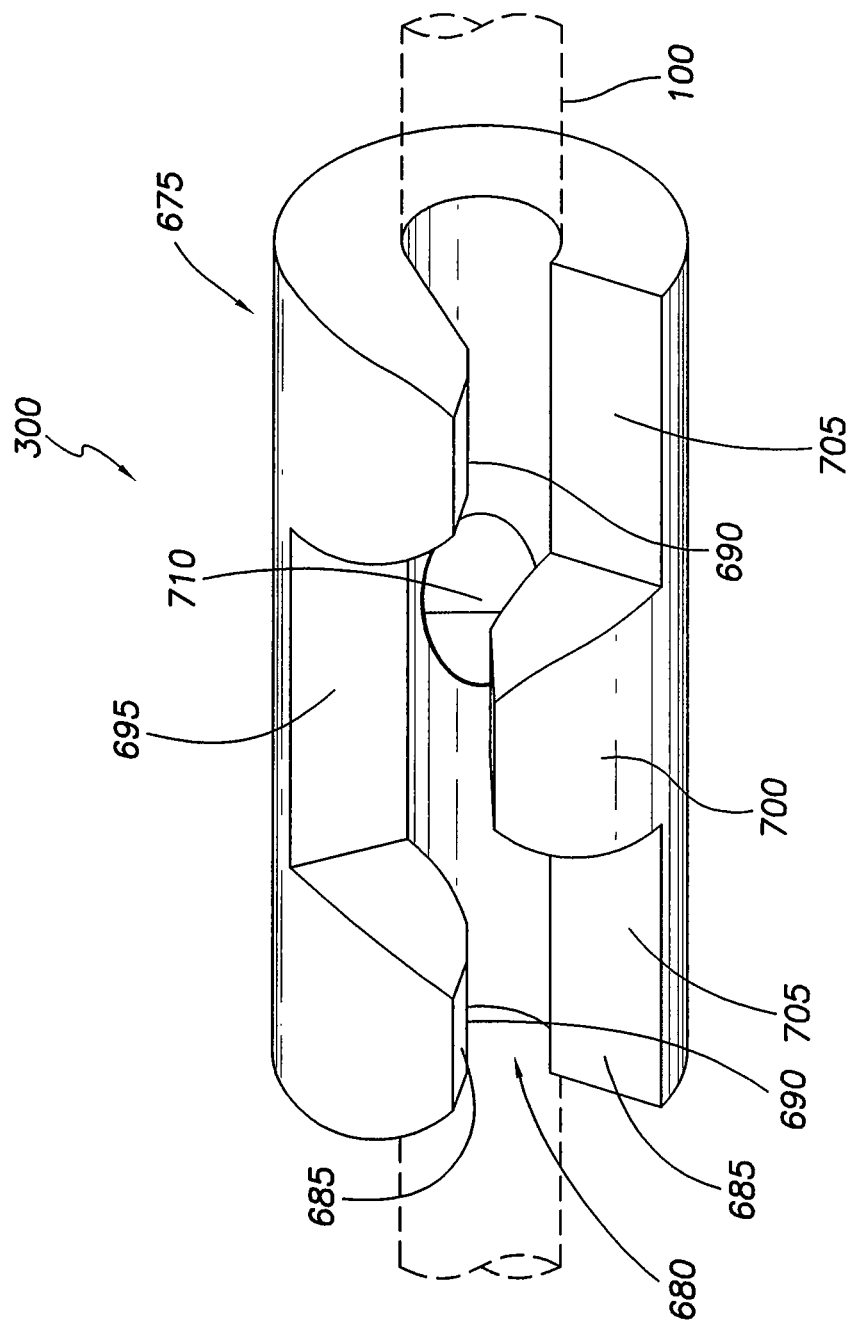
FIG. 19 is an isometric view of a side loader crimp slug.

FIG. 19 is an isometric view of a side loader crimp slug 300. As depicted in FIG. 19, the crimp 300 includes a cylindrical head 675 with a longitudinal slot 680 that defines two opposed edges 685. One edge 685 includes two end projections 690 separated by a single central recess 695. The other edge 685 includes a single centered projection 700. The two edges complement each other in that when the edges 685 are forced together when the crimp 300 is crimped down on an exposed conductor 100 extending through the cylindrical head 675, the single centered projection 700 is received in the single central recess 695, and the end projections 690 are received in the open spaces 705 adjacent the centered projection 700.

As illustrated in FIG. 19, the exposed conductor 100 is received in the trough of the cylindrical head 675. Specifically, one of the edges 685 is inserted under the exposed conductor 100 to cause the conductor to be received in the trough of the head 675.

The crimp 300 could be added to the conductor before the conductor is wound into the lead body as described above with respect to FIGS. 1-10. A hole 710 in the crimp 300 could then be used to add a post to the crimp. The post could be added by stamping a flat pattern and welding the post into the hole.

Alternatively, the crimp 300 could be made as shown and then crimped onto the conductor subsequent to the conductor being wound into the body as described above with respect to FIGS. 1-10. After crimping a post could be placed in the hole and welded on. This post, similar to the tails described above, would be used to aid in welding and alignment to a slot or window in the ring electrode.

In other embodiments, the crimp 300 will not have the hole 710 depicted in FIG. 19. The crimp is instead welded to the ring electrode via welding and direct intimate contact between the outer surface of the crimp and the interior of the ring electrode.

Figure 20A:
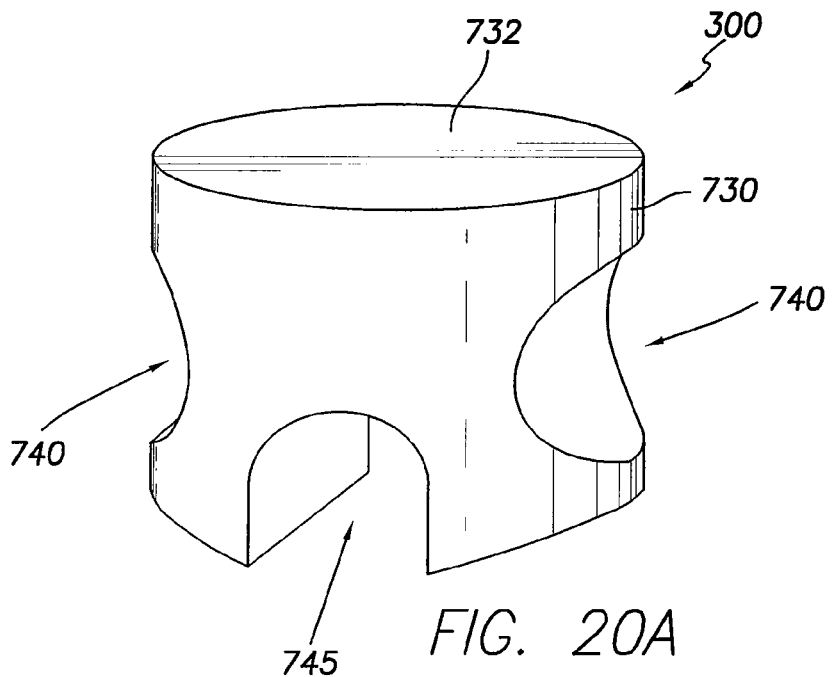
FIGS. 20A and 20B are, respectively, isometric and side views of a notched cylindrical crimp slug.
Figure 20B:
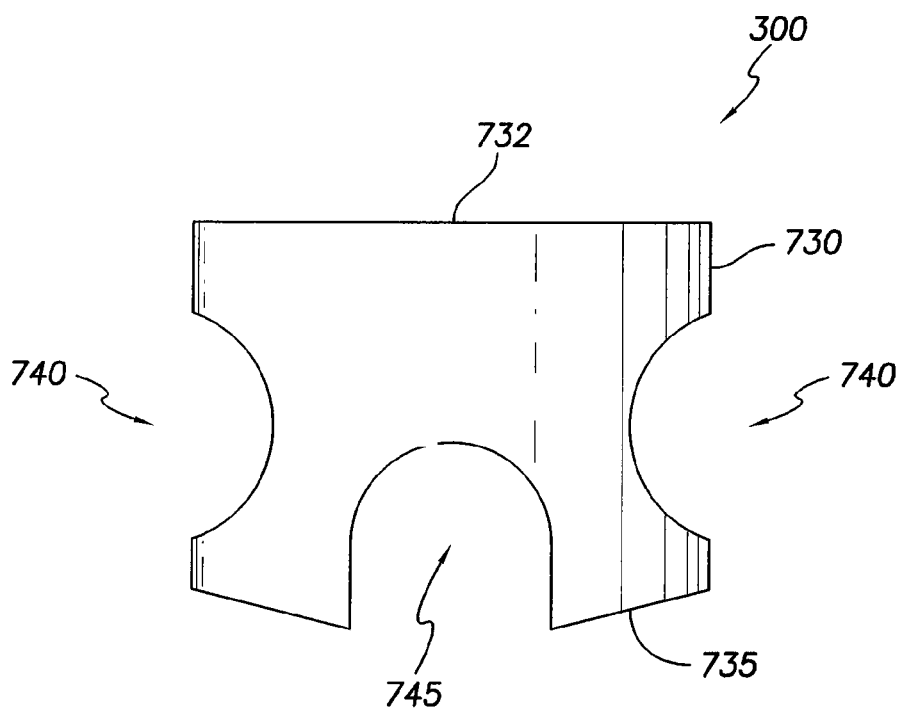

FIGS. 20A and 20B, which are, respectively, isometric and side views of another crimp slug 300. As shown in FIGS. 20A and 20B, the crimp slug 300 includes a generally cylindrical side surface 730, a planar upper surface 732, and a semi-sloped bottom surface 735. A pair of notches or recesses 740 are defined in opposite sides of the cylindrical side surface 730, the recesses being configured to be engaged by a crimping tool. A notch or recess 745 is defined in the bottom surface 735, the recess being configured to receive a conductor 100.

Figure 20C:
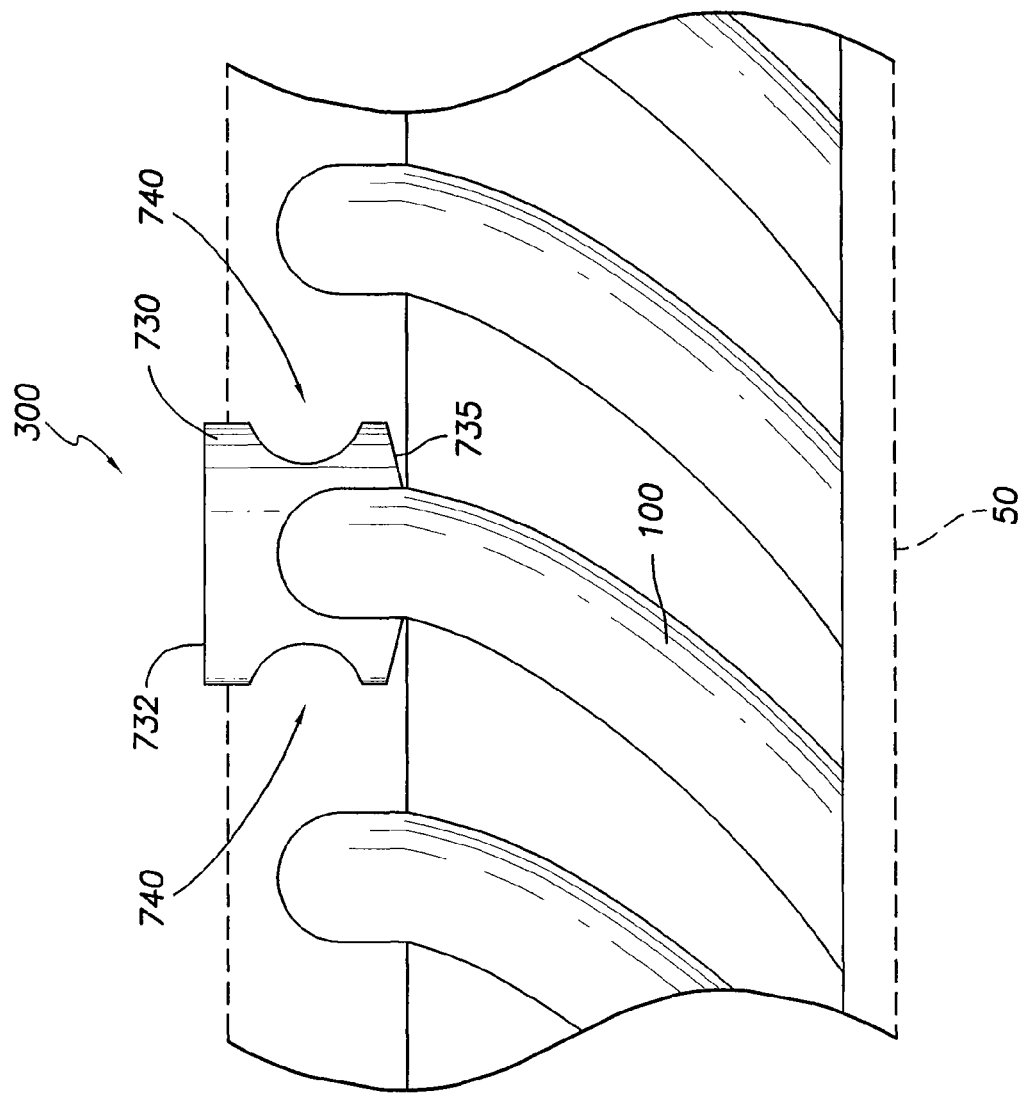
FIG. 20C is a side view of a portion of a lead, wherein the crimp slug of FIGS. 20A and 20B is coupled to a conductor.

FIG. 20C is a side view of a portion of a lead body 50, wherein the crimp slug 300 of FIGS. 20A and 20B is coupled to a conductor 100. As depicted in FIG. 20C, the conductor 100 is received in the bottom recess 745, and a crimp tool is applied to the side recesses 740 to crimp the bottom recess 745, causing the crimp slug 300 to be coupled to the conductor 100. The crimp slug 300 can be attached to a pre-wound conductor, access to the conductor 100 being achieved by ablating a window. Alternatively, the crimp slug 300 can be added to the conductor 100 prior to the addition of the polymer layer in which the conductor ends up being imbedded. Regardless of when the crimp slug 300 is attached to the conductor, the crimp can then be welded to a split ring electrode or a slotted ring electrode.

Figure 21A:
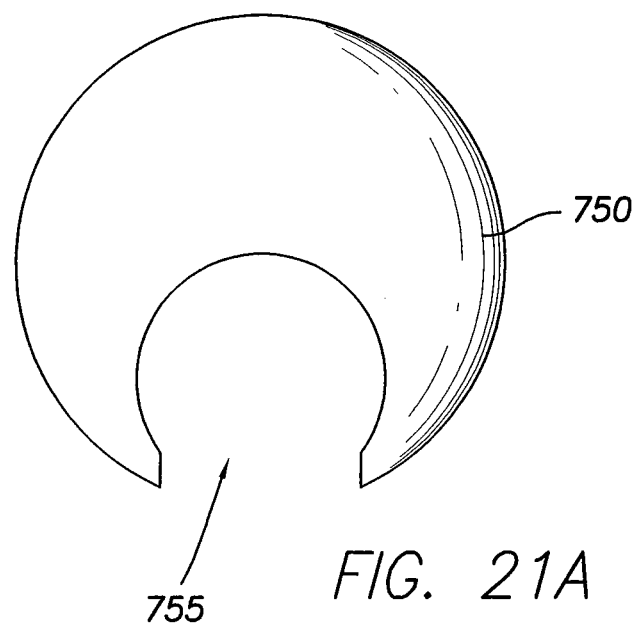
FIGS. 21A and 21B, which are, respectively, isometric and side views of a notched spherical crimp slug.
Figure 21B:
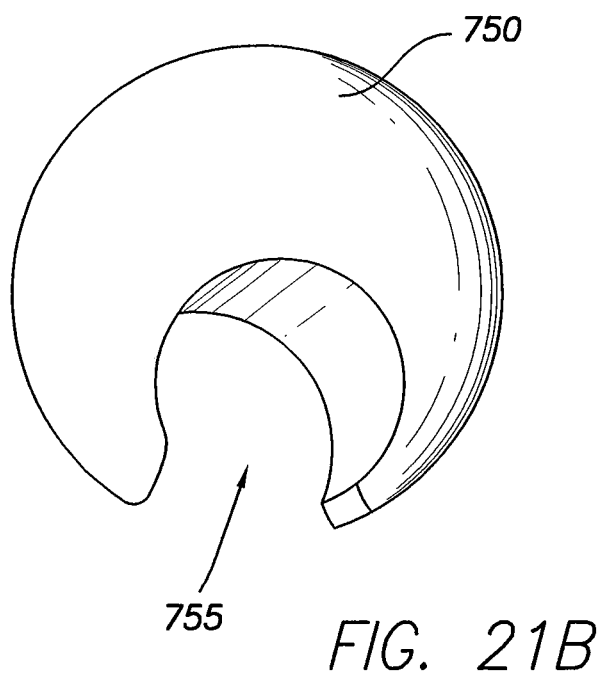

FIGS. 21A and 21B, which are, respectively, isometric and side views of another crimp slug 300. As illustrated in FIGS. 21A and 21B, the crimp slug 300 includes a generally spherical outer surface 750 and a notch or recess 755 defined in the spherical outer surface 750, the recess being configured to receive a conductor 100.

Similar to the crimp 300 of FIGS. 20A-20C, the crimp 300 of FIGS. 21A-21B can be coupled to a conductor 100. Specifically, the conductor 100 is received in the recess 755, and a crimp tool is applied to the outer spherical surface 750 to crimp the recess 755, causing the crimp slug 300 to be coupled to the conductor 100. The crimp slug 300 can be attached to a pre-wound conductor, access to the conductor 100 being achieved by ablating a window. Alternatively, the crimp slug 300 can be added to the conductor 100 prior to the addition of the polymer layer in which the conductor ends up being imbedded. Regardless of when the crimp slug 300 is attached to the conductor, the crimp can then be welded to a split ring electrode or a slotted ring electrode.

Figure 22:
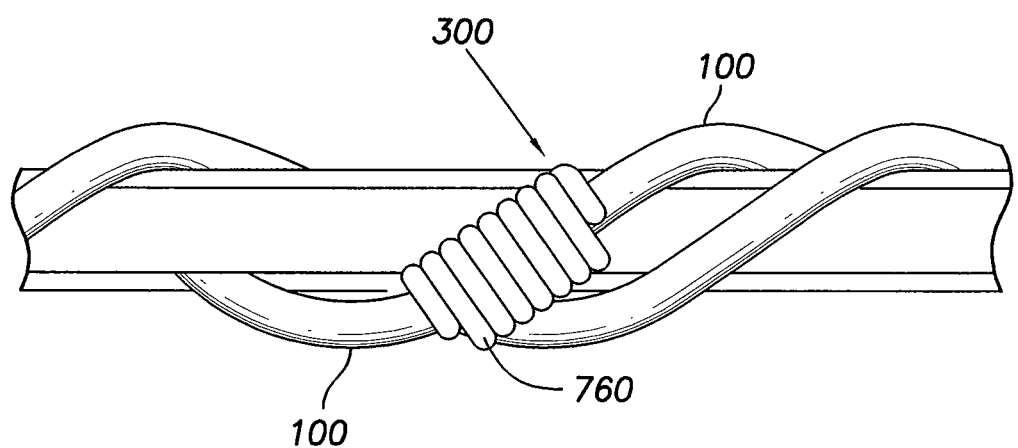
FIG. 22 is a plan view of a twisted micro wire crimp on a conductor.

As indicated in FIG. 22, which is a plan view of a twisted crimp 300 on a conductor 100, the crimp slug 300 may be in the form of a micro wire or coil 760 twisted onto the conductor 100 and then crimped flat on the conductor. The twisted crimp 300 can then be welded to a ring electrode 80.

Most, if not all, of the above-described crimp slugs 300 can be added to the conductor 100 subsequent to the assembly of the conductor into the lead body 50. Also, most, if not all, of the above-described crimp slugs 300 can be added to the conductor 100 prior to the conductor 100 being assembled into the lead body 10, for example, where the crimp slugs 300 are applied to the conductor 100 and the crimp slug equipped conductor is stored in discrete lengths or in bulk on a spool until needed for assembly into the lead body 50. Also, in another embodiment, the crimp slugs 300 may be added to the conductor 100 during the manufacture of the lead body 50 immediately before the conductor 100 is wound into the lead body.

The following crimp slugs 300 are especially useful in the context of applying the crimp slugs 300 to a conductor 100 prior to the conductor 100 being assembled into the lead body 50. Specifically, the crimps 300 discussed below are attached to the conductor 100 and the crimp equipped conductor 100 is stored in discrete lengths or in bulk on spools until needed for assembly into a lead body. For example, when assembling the lead body 50 depicted in FIG. 4, a conductor 100 with crimps 300 already mounted along the length of the conductor 100 is removed from a spool and wound about the inner liner 130.

As can be understood from FIGS. 23A and 23B, which are, respectively, a side view of a lead body 50 and an enlarged side view of the same lead body at a location of a crimp 300, in the context of preassembling the crimps 300 onto the conductor 100 and storing the conductor in discrete lengths or on a spool, the crimps 300 can be added at a evenly spaced defined distance on a conductor 100. The spacing of the crimps 300 on the conductors 100 could be such that when multiple conductors are wound onto the liner 130, the crimp patterns are appropriately offset to create a specified spacing between the crimps. For example, as indicated in FIG. 23A, four conductors 100, 105, 110, 111 are wound about the liner 130 and the crimps 300 on the conductors are spaced such that the spacing X between adjacent crimps 300 is approximately 15 mm apart, the pattern repeating approximately every 90 cm.

FIGS. 24A and 24B are, respectively, a plan view of a helical wound crimp 300 and a plan view of the same crimp 300 mounted on a conductor 100. As indicated in FIGS. 24A and 24B, such a helical wound crimp 300 may have coils 800 with a variable pitch. Specifically, part of the crimp 300 has a tight pitch region 805 that can act as a strong location for welding to a ring electrode and an open pitch region 810 that can act as a conformal strain relief. In one embodiment, the coils 800 of the tight pitch region 805 is welded to the ring electrode 80. In another embodiment, a portion of the crimp 300 is welded to the ring electrode 80, wherein the portion of the crimp 300 is a coil 800 that is pulled outward to form a tab to be welded to the electrode or an end of the wire forming the coils 80 is pulled outward to form a table to be welded to the electrode. The resulting tab could be welded to the slot in the ring electrode, similar to methods described above.

To mount the helical crimp 300 on the conductor 100, the conductor is threaded through the helical crimp 300 when the helical crimp is in a cylindrical shape. Once positioned as desired, the helical crimp 300 is crimped onto the conductor 100 to cause the crimp to conform to the conductor.

Figure 25A:
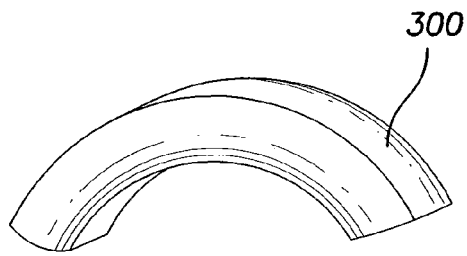
FIGS. 25A-25C are, respectively, side, inner and outer views of a helically shaped crimp.
Figure 25B:
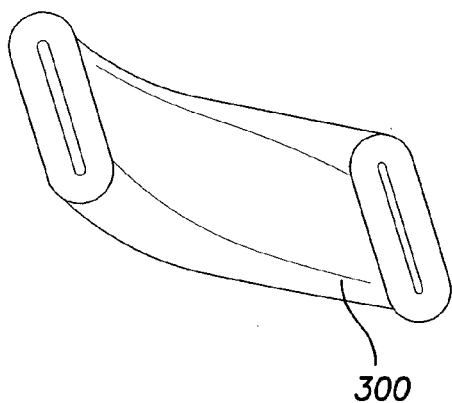
Figure 25C:
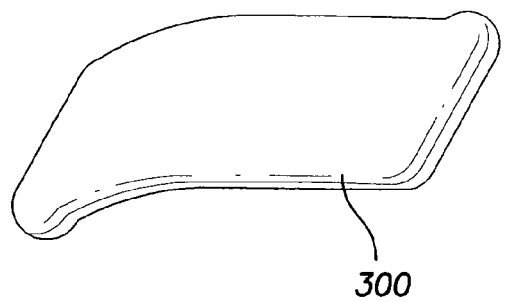
Figure 25D:
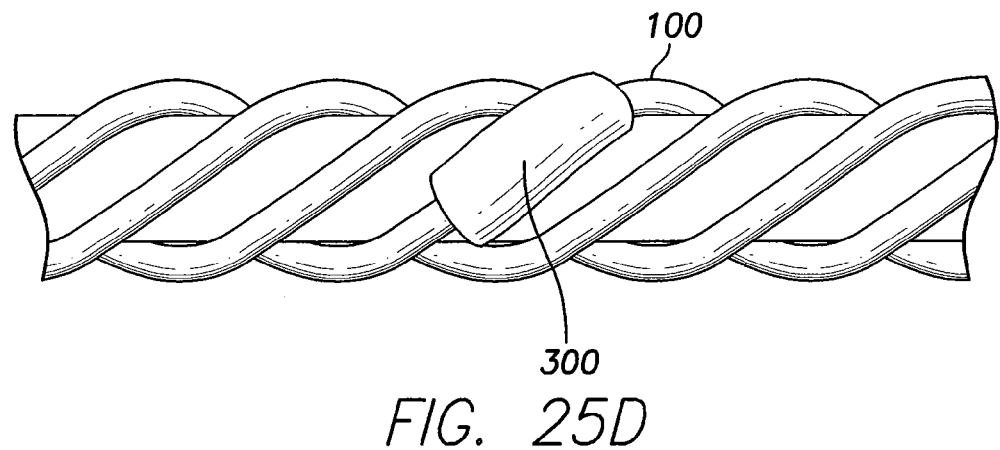
FIGS. 25D-25E are, respectively, the crimp on a conductor and a crimp-equipped conductor assembled into a lead body, the conductor would be fed through the helical crimp.
Figure 25E:
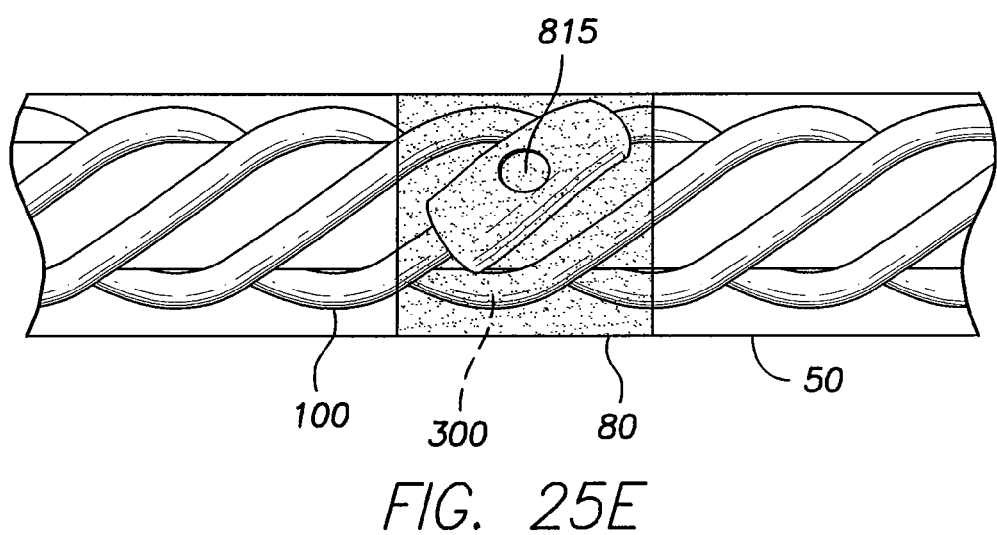

FIGS. 25A-25C illustrate, respectively, side, inner and outer views of a helically shaped crimp 300. As can be understood from FIGS. 25A-25C, the crimp 300 is a solid tube that is helically shaped. The helical crimp 300 of FIGS. 25A-25C would work similar to the helical spring crimp 300 of FIGS. 24A-24B. Specifically, as can be understood from FIGS. 25D-25E, which are, respectively, the crimp 300 on a conductor and a crimp-equipped conductor assembled into a lead body, the conductor 100 would be fed through the helical crimp 300. The crimp 300 would then be crimped onto the conductor 100 such that the crimp 100 would match the natural pitch of the final wound cable. The helical crimp outside diameter would match the inside diameter of the ring electrode 80, creating a large surface for welding. The crimp 300 would be welded to a ring electrode 80 through a hole 815 for visualization in the crimp 300.

All crimp concepts disclosed herein apply to conductors that are solid wire or multi-filar conductors and conductors that are wound or braided.

Although the present invention has been described with reference to preferred embodiments, persons skilled in the art will recognize that changes may be made in form and detail without departing from the spirit and scope of the invention.

What is claimed is:

1. An implantable medical lead comprising:
   a longitudinally extending body having a distal end and a proximal end;
   a ring electrode on the body near the distal end;
   a lead connector end operably coupled to the proximal end of the body;
   a tubular braid arrangement having an electrical conductor braided with an electrical nonconductor;
   wherein the electrical conductor extends between the lead connector end and the ring electrode; and
   a crimp slug looped around the electrical conductor and cinched about the electrical conductor, the crimp slug crimped to secure the electrical conductor onto the crimp slug;
   wherein the ring electrode comprises a cylindrical wall and a seam extending proximal to distal along the wall, the seam formed by a first wall edge extending proximal to distal and a second wall edge extending proximal to distal, the wall edges being opposed and brought together to form the seam, each wall edge having a notch such that, when the wall edges are brought together to form the seam, the notches form a window extending through the wall.

2. The lead of claim 1, wherein the crimp slug is positioned at the window.

3. The lead of claim 1, wherein the crimp slug is welded to the ring electrode to be electrically and mechanically coupled to the ring electrode, the weld being located at the window.

* * * * *